(12) United States Patent
Bhat et al.

(10) Patent No.: US 11,389,454 B2
(45) Date of Patent: Jul. 19, 2022

(54) TABLET COMPOSITIONS

(71) Applicants: Celgene Corporation, Summit, NJ (US); Agios Pharmaceuticals, Inc., Cambridge, MA (US)

(72) Inventors: Sreenivas S. Bhat, Kendall Park, NJ (US); Scott Burnside, Wilmington, NC (US); Darshan Parikh, Bridgewater, NJ (US); Chong-Hui Gu, Waban, MA (US); Syed Altaf, Lexington, MA (US)

(73) Assignees: CELGENE CORPORATION, Summit, NJ (US); SERVIER PHARMACEUTICALS LLC, Boston, MA (US)

( * ) Notice: Subject to any disclaimer, the term of this patent is extended or adjusted under 35 U.S.C. 154(b) by 0 days.

(21) Appl. No.: 15/697,199

(22) Filed: Sep. 6, 2017

(65) Prior Publication Data
US 2018/0064715 A1    Mar. 8, 2018

Related U.S. Application Data

(60) Provisional application No. 62/535,162, filed on Jul. 20, 2017, provisional application No. 62/384,643, filed on Sep. 7, 2016.

(51) Int. Cl.
*A61K 31/53* (2006.01)
*A61K 9/20* (2006.01)
*A61K 9/28* (2006.01)

(52) U.S. Cl.
CPC ............ *A61K 31/53* (2013.01); *A61K 9/2009* (2013.01); *A61K 9/2013* (2013.01); *A61K 9/2027* (2013.01); *A61K 9/2031* (2013.01); *A61K 9/2054* (2013.01); *A61K 9/2059* (2013.01); *A61K 9/2077* (2013.01); *A61K 9/2095* (2013.01); *A61K 9/28* (2013.01)

(58) Field of Classification Search
CPC ...... A61K 9/28; A61K 9/2027; A61K 9/2095; A61K 31/53; A61K 9/2031; A61K 9/2013; A61K 9/2077; A61K 9/2054; A61K 9/2059; A61K 9/2009
See application file for complete search history.

(56) References Cited

U.S. PATENT DOCUMENTS

| | | | | |
|---|---|---|---|---|
| 6,036,975 | A | * | 3/2000 | Gebhard-Hansen ... A61K 9/205 424/465 |
| 7,132,114 | B2 | * | 11/2006 | Daggy ................. A61K 9/0056 424/464 |
| 9,512,107 | B2 | | 12/2016 | Cianchetta et al. |
| 9,656,999 | B2 | | 5/2017 | Cianchetta et al. |

(Continued)

FOREIGN PATENT DOCUMENTS

| | | | |
|---|---|---|---|
| WO | WO 2015/017821 A2 | * | 2/2015 |
| WO | WO 2015/018060 A1 | | 2/2015 |

(Continued)

OTHER PUBLICATIONS

IDHIFA label issued Aug. 2017, available online at URL:<https://www.accessdata.fda.gov/drugsatfda_docs/label/2017/209606s0001b1.pdf> (17 pages).

*Primary Examiner* — Hong Yu
(74) *Attorney, Agent, or Firm* — Jones Day

(57) ABSTRACT

Provided herein is a tablet comprising 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol or a pharmaceutically acceptable salt thereof.

4 Claims, 9 Drawing Sheets

(56) References Cited

U.S. PATENT DOCUMENTS

| | | |
|---|---|---|
| 9,694,013 B2 | 7/2017 | Agresta |
| 9,724,350 B2 | 8/2017 | Travins |
| 9,732,062 B2 | 8/2017 | Cianchetta et al. |
| 9,738,625 B2 | 8/2017 | Agresta et al. |
| 9,751,863 B2 | 9/2017 | Zhang |
| 2003/0158154 A1* | 8/2003 | Fleshner-Barak ... A61K 31/663 514/89 |
| 2007/0010478 A1* | 1/2007 | Sikic .................... A61K 31/337 514/49 |
| 2011/0111018 A1* | 5/2011 | Ashraf ................. A61K 9/2027 424/452 |
| 2012/0046330 A1* | 2/2012 | Alargova ............. A61K 9/1623 514/414 |
| 2016/0089374 A1* | 3/2016 | Agresta ................. A61K 31/53 514/245 |
| 2016/0354315 A1* | 12/2016 | Li ......................... A61K 9/209 |
| 2017/0157132 A1 | 6/2017 | Wu et al. |
| 2017/0246174 A1 | 8/2017 | Amatangelo et al. |
| 2017/0266193 A1 | 9/2017 | Agresta |
| 2017/0298045 A1 | 10/2017 | Cianchetta et al. |
| 2017/0305885 A1 | 10/2017 | Agresta et al. |

FOREIGN PATENT DOCUMENTS

| | | |
|---|---|---|
| WO | WO 2016/126798 A1 | 8/2016 |
| WO | WO 2017/066599 A1 | 4/2017 |
| WO | WO 2017/066611 A1 | 4/2017 |

* cited by examiner

TABLET COMPOSITIONS

RELATED APPLICATIONS

This application claims the benefit of U.S. Provisional Application No. 62/384,643, filed Sep. 7, 2016 and U.S. provisional application No. 62/535,162, filed Jul. 20, 2017, the disclosures of each of which are incorporated by reference in their entireties.

FIELD

Provided herein are tablet compositions comprising 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol or pharmaceutically acceptable salts thereof. In certain embodiments, the tablet is used as a medicament for treating a proliferative disease, such as cancer.

BACKGROUND ART

It has been reported that 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol or a pharmaceutically acceptable salt thereof is effective in treating proliferative diseases, including cancers. See US Publication No. US 2013/0190287; US 2016/0089374 and WO 2015/017821.

There is a need to develop tablet formulations comprising 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol that have good manufacturability, dissolution, stability and bioavailability.

SUMMARY

Provided herein is a tablet composition comprising 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol or a pharmaceutically acceptable salt thereof (Compound 1) as an active agent, one or more intragranular excipients and one or more extragranular excipients. In one embodiment, the tablet composition comprises 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol or 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate as an active agent, one or more intragranular excipients and one or more extragranular excipients. In one embodiment, the tablet composition comprises a 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate as an active agent, one or more intragranular excipients and one or more extragranular excipients.

In certain embodiments, the active agent used in the tablet compositions is a solid form of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate salt. In one embodiment, the tablet composition comprises polymorph Form 3 of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate as an active agent, one or more intragranular excipients and one or more extragranular excipients.

In one embodiment, intragranular excipients comprise a diluent, a binder, a solubility enhancer, disintegrant, a glidant and a lubricant. In one embodiment, the extragranular excipients comprise a diluent, disintegrant, a glidant, a lubricant, and a coating agent.

In certain embodiments, the tablets provided herein are coated tablets of 25 mg, 50 mg, 100 mg and 150 mg strength of Compound 1. In certain embodiments, the tablets provided herein are coated tablets of 25 mg, 50 mg, 100 mg and 150 mg strength of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol.

In certain embodiment, provided herein is a method for preparing a tablet comprising Compound 1. In certain embodiments, the method comprises blending Compound 1 with an intragranular excipient and an extragranular excipient and compressing with a compression tooling.

In one embodiment, the method comprises mixing Compound 1, a diluent, a binder, a solubility enhancer, a disintegrant and a glidant in a pre-blending step to obtain a pre-blend, mixing the pre-blend with a lubricant to obtain a lubricated pre-blend, dry granulating to obtain compacted granules which are then mixed with extra-granular excipients including a diluent, a disintegrant, a glidant and a lubricant to obtain the final blend. The final blend is then compressed with a compression tooling to obtain a tablet. In certain embodiments, the tablet is coated with a coating agent.

In certain embodiments, provided herein is a tablet comprising about 15 to about 50% Compound 1 as an active ingredient. In certain embodiments, provided herein is a tablet comprising about 20, 25 or 30% by weight of Compound 1 as an active ingredient based on the total weight of the tablet.

In certain embodiments, provided herein are methods of treating hematologic malignancies or solid tumors, each characterized by the presence of a mutant allele of IDH2 comprising administering a tablet provided herein. Also provided herein is Compound 1 for use in such methods.

In one embodiment, the hematologic malignancy is selected from acute myelogenous leukemia (AML), myelodysplastic syndrome (MDS), chronic myelomonocytic leukemia (CMML), myeloid sarcoma, multiple myeloma, lymphoma (e.g., T-cell lymphoma or B-cell lymphoma), angioimmunoblastic T-cell lymphoma (AITL) and blastic plasmacytoid dendritic cell neoplasm, each characterized by the presence of a mutant allele of IDH2. In one embodiment, the hematologic malignancy is selected from acute myelogenous leukemia (AML), myelodysplastic syndrome (MDS), chronic myelomonocytic leukemia (CMML), myeloid sarcoma, multiple myeloma, lymphoma (e.g., T-cell lymphoma or B-cell lymphoma), angioimmunoblastic T-cell lymphoma (AITL), blastic plasmacytoid dendritic cell neoplasm, and myeloproliferative neoplasm (MPN), each characterized by the presence of a mutant allele of IDH2.

In one embodiment, the solid tumor is selected from glioma, melanoma, chondrosarcoma, and cholangiocarcinoma, each characterized by the presence of a mutant allele of IDH2.

DETAILED DESCRIPTION

Figure 1:
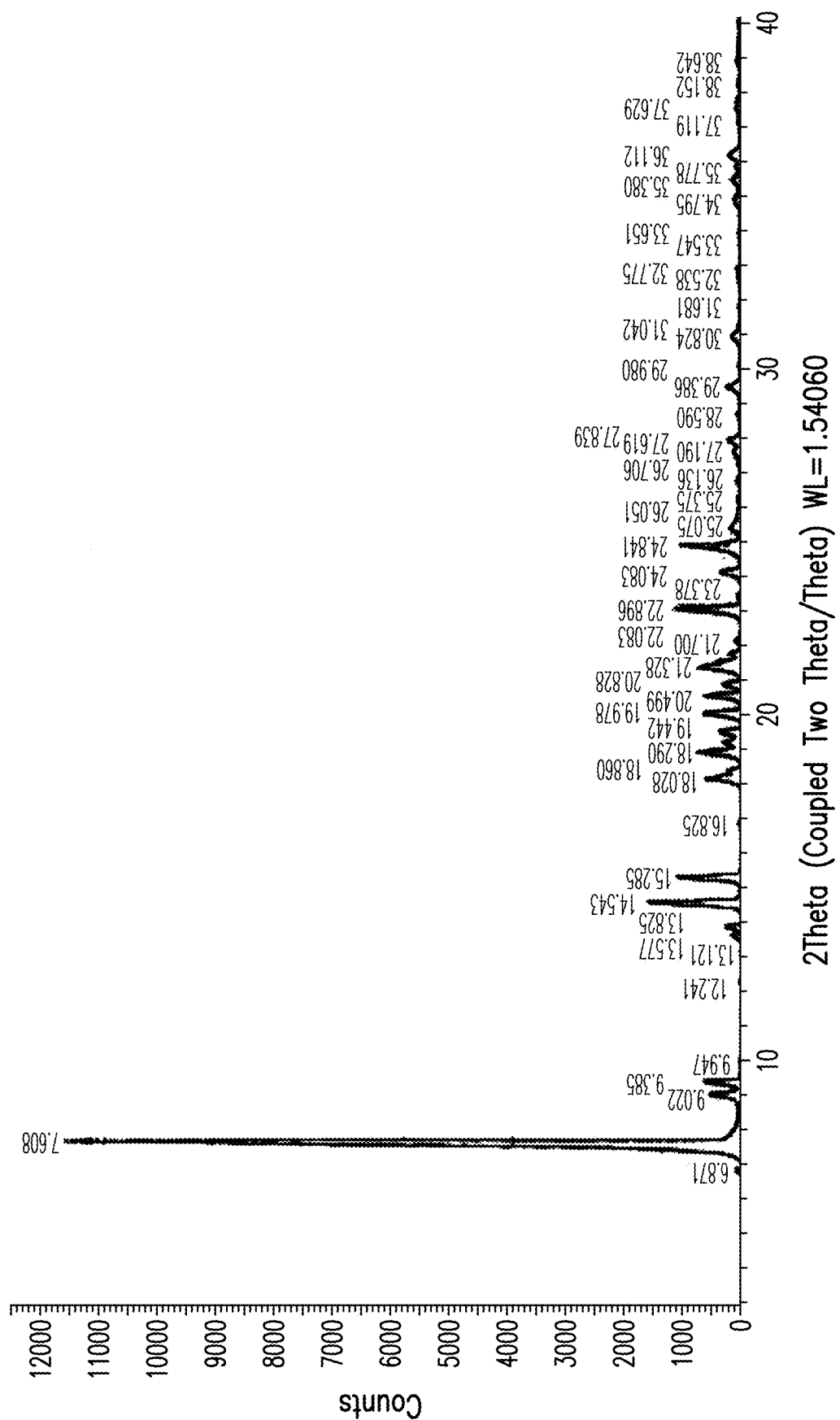
FIG. 1 is an X-ray powder diffractogram (XRPD) of compound 1 Form 3.

The details of construction and the arrangement of components set forth in the following description or illustrated in the drawings are intended to describe non-limiting embodiments. Other embodiments and different ways to practice the invention are expressly included. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Definitions

As used above, and throughout the description of the invention, the following terms, unless otherwise indicated, shall be understood to have the following meanings.

As used in this application, the singular form "a", "an" and "the" include plural references unless the context clearly dictates otherwise. For example, the term "an intragranular excipient" includes one or more intragranular excipients.

"Compound 1" is meant to describe 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol or a pharmaceutically acceptable salt thereof. In one embodiment, the pharmaceutically acceptable salt is a methanesulfonate salt also known as mesylate salt of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol, including solid forms thereof.

The term "solid form" refers a crystal form or an amorphous form or a mixture thereof of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol or a methanesulfonate salt thereof. Exemplary solid forms of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol and its methanesulfonate salt are described in WO 2015/018060, WO 2015/017821 and PCT/US2016/016335, each of which is incorporated by reference in its entirety.

As used herein, the terms "inhibit" or "prevent" include both complete and partial inhibition and prevention. An inhibitor may completely or partially inhibit the intended target.

The term "treat" means decrease, suppress, attenuate, diminish, arrest, or stabilize the development or progression of a disease/disorder (i.e., a cancer such as glioma, melanoma, chondrosarcoma, or cholangiocarcinoma, acute myelogenous leukemia (AML), myelodysplastic syndrome (MDS), chronic myelomonocytic leukemia (CMML), lymphoma (e.g., T-cell lymphoma) or myeloproliferative neoplasm (MPN)), lessen the severity of the disease/disorder (i.e., a cancer selected from solid tumor, acute myelogenous leukemia (AML), myelodysplastic syndrome (MDS), chronic myelomonocytic leukemia (CMML), lymphoma (e.g., T-cell lymphoma), or myeloproliferative neoplasm (MPN)), each characterized by the presence of a mutant allele of IDH2, or improve the symptoms associated with the disease/disorder (i.e., a cancer such as glioma, melanoma, chondrosarcoma, or cholangiocarcinoma, acute myelogenous leukemia (AML), myelodysplastic syndrome (MDS), chronic myelomonocytic leukemia (CMML), lymphoma (e.g., T-cell lymphoma) or myeloproliferative neoplasm (MPN)), lessen the severity of the disease/disorder (i.e., a cancer selected from solid tumor, acute myelogenous leukemia (AML), myelodysplastic syndrome (MDS), chronic myelomonocytic leukemia (CMML), lymphoma (e.g., T-cell lymphoma) or myeloproliferative neoplasm (MPN)), each characterized by the presence of a mutant allele of IDH2).

As used herein, and unless otherwise specified, the terms "prevent," "preventing" and "prevention" refer to the prevention of the onset, recurrence or spread of a disease or disorder, or of one or more symptoms thereof. The terms "prevent," "preventing" and "prevention" contemplate an action that occurs before a patient begins to suffer from the specified disease or disorder or symptoms thereof, which inhibits or reduces the severity of the disease or disorder.

As used herein, and unless otherwise indicated, the terms "manage," "managing" and "management" encompass preventing the recurrence of the specified disease or disorder in a patient who has already suffered from the disease or disorder, or lengthening the time that a patient who has suffered from the disease or disorder remains in remission. The terms encompass modulating the threshold, development or duration of the disease or disorder, or changing the way that a patient responds to the disease or disorder.

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

The terms "subject," "patient," "subject in need thereof," and "patient in need thereof" are herein used interchangeably and refer to a living organism suffering from one or more of the diseases described herein (e.g., AML) that can be treated by administration of a composition described herein. Non-limiting examples of organisms include humans, other mammals, bovines, rats, mice, dogs, monkeys, goat, sheep, cows, deer, and other non-mammalian animals. In embodiments, a subject is human. A human subject can be between the ages of about 1 year old to about 100 years old. In embodiments, subjects herein can be characterized by the disease being treated (e.g., a "AML subject", a "cancer subject", or a "leukemia subject").

A "pharmaceutically acceptable excipient," refers to a substance that aids the administration of an active agent to a subject by for example modifying the stability of an active agent or modifying the absorption by a subject upon administration. A pharmaceutically acceptable excipient typically has no significant adverse toxicological effect on the patient. Examples of pharmaceutically acceptable excipients include, for example bulking agents, buffers, binders, fillers, disintegrants, lubricants, coatings, sweeteners, flavors, fatty acid esters, hydroxymethycellulose, polyvinyl pyrrolidine, and colors, and the like. One of skill in the art will recognize that other pharmaceutical excipients known in the art are useful in the present invention and include those listed in for example the *Handbook of Pharmaceutical Excipients*, Rowe R. C., Shesky P. J., and Quinn M. E., 6$^{th}$ Ed., The Pharmaceutical Press, RPS Publishing (2009). The terms "bulking agent", and "buffer" are used in accordance with the plain and ordinary meaning within the art.

The term "intragranular excipients" refers to ingredients that are incorporated in the formulation prior to granulation, i.e., ingredients that are located internally in the granule structure.

The term "extragranular excipients" refers to ingredients that are incorporated after granulation, i.e. ingredients that are located externally to the granule structure.

As used herein, "administer" or "administration" refers to the act of physically delivering a substance as it exists outside the body into a subject. Administration includes all forms known in the art for delivering therapeutic agents, including but not limited to oral, topical, mucosal, injections, intradermal, intravenous, intramuscular delivery or other method of physical delivery described herein or known in the art (e.g., implantation of a slow-release device, such as a mini-osmotic pump to a subject; liposomal formulations; buccal; sublingual; palatal; gingival; nasal; vaginal; rectal; intra-arteriole; intraperitoneal; intraventricular; intracranial; or transdermal).

The term "co administering" as used herein with respect to an additional cancer therapeutic agents means that the additional cancer therapeutic agent may be administered prior to, consecutively with, or following the administration of a composition provided herein. In such combination therapy treatment, the second therapeutic agent(s) is administered by conventional methods.

As used herein, the term "about" means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

1. Compound

In one embodiment, Compound 1 for use in the tablet compositions herein is 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol having the following formula:

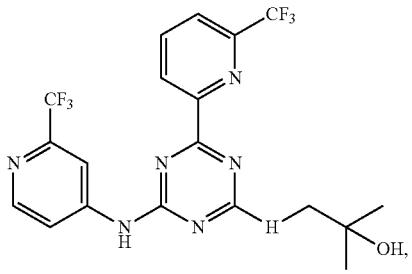

or a pharmaceutically acceptable salt thereof (Compound 1).

In one embodiment, Compound 1 is 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate.

In one embodiment, Compound 1 is a solid form of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate. Exemplary solid forms of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol and 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate are described in WO 2015/018060 and WO 2015/017821 and PCT/US2016/016335, each of which is incorporated by reference in its entirety.

In one embodiment, Compound 1 is polymorph Form 3 of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate.

Exemplary methods for synthesis of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol and 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate are described in US published application US-2013/0190287 and U.S. Provisional Application No. 62/201,546. Exemplary methods for synthesis of solid forms of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate are described in WO 2015/018060, WO 2015/017821 and PCT/US2016/016335, each of which is incorporated by reference in its entirety.

In certain embodiments, the tablet compositions provided herein comprise Compound 1 in about 15% to about 50% by weight based on total weight of the tablet. In certain embodiments, the tablet compositions provided herein comprise Compound 1 in about 15% to about 40% by weight based on total weight of the tablet. In certain embodiments, the tablet compositions provided herein comprise Compound 1 in about 20%, about 25% or about 30% by weight based on total weight of the tablet. In certain embodiments, the tablet compositions provided herein comprise Compound 1 in an amount of about 20% by weight based on total weight of the tablet. In certain embodiments, the tablet compositions provided herein comprise Compound 1 in an amount of about 25% by weight based on total weight of the tablet. In certain embodiments, the tablet compositions provided herein comprise Compound 1 in an amount of about 30% by weight based on total weight of the tablet.

In certain embodiments, the tablet compositions provided herein comprise 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol in about 15% to about 50% by weight based on total weight of the tablet. In certain embodiments, the tablet compositions provided herein comprise 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol in about 15% to about 40% by weight based on total weight of the tablet. In certain embodiments, the tablet compositions provided herein comprise 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol in about 20%, about 25% or about 30% by weight based on total weight of the tablet.

2. Polymorph Form 3

In one embodiment, the tablets provided herein comprise polymorph Form 3 of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate.

In one embodiment, polymorph Form 3 of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate was prepared by contacting a solution of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol in acetone with methanesulfonic acid (MSA)/acetone solution.

In certain embodiments, polymorph Form 3 of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate is characterized by the X-ray powder diffraction (XRPD) pattern shown in FIG. 1, and data shown in Table A, obtained using CuKa radiation. In a particular embodiment, the polymorph is characterized by one or more of the peaks taken from FIG. 1, as shown in Table A. For example, the polymorph is characterized by one or two or three or four or five or six or seven or eight or nine or ten of the peaks shown in Table A.

TABLE A

| Angle 2-Theta° | Intensity % |
| --- | --- |
| 7.5 | 100.0 |
| 9.0 | 16.5 |
| 9.3 | 27.2 |
| 14.5 | 48.5 |
| 15.2 | 17.2 |
| 18.0 | 17.0 |
| 18.8 | 32.6 |
| 19.9 | 18.7 |
| 21.3 | 19.3 |
| 24.8 | 33.8 |

In another embodiment, Form 3 is characterized by the peaks identified at 2θ angles of 7.5, 9.3, 14.5, 18.8, 21.3, and 24.8°. In a further embodiment, Form 3 is characterized by the peaks are identified at 2θ angles of 7.5, 14.5, 18.8, and 24.80. In another, embodiment, Form 3 is characterized by the peaks identified at 2θ angles of 7.5, 14.5, and 24.8°.

Figure 2:
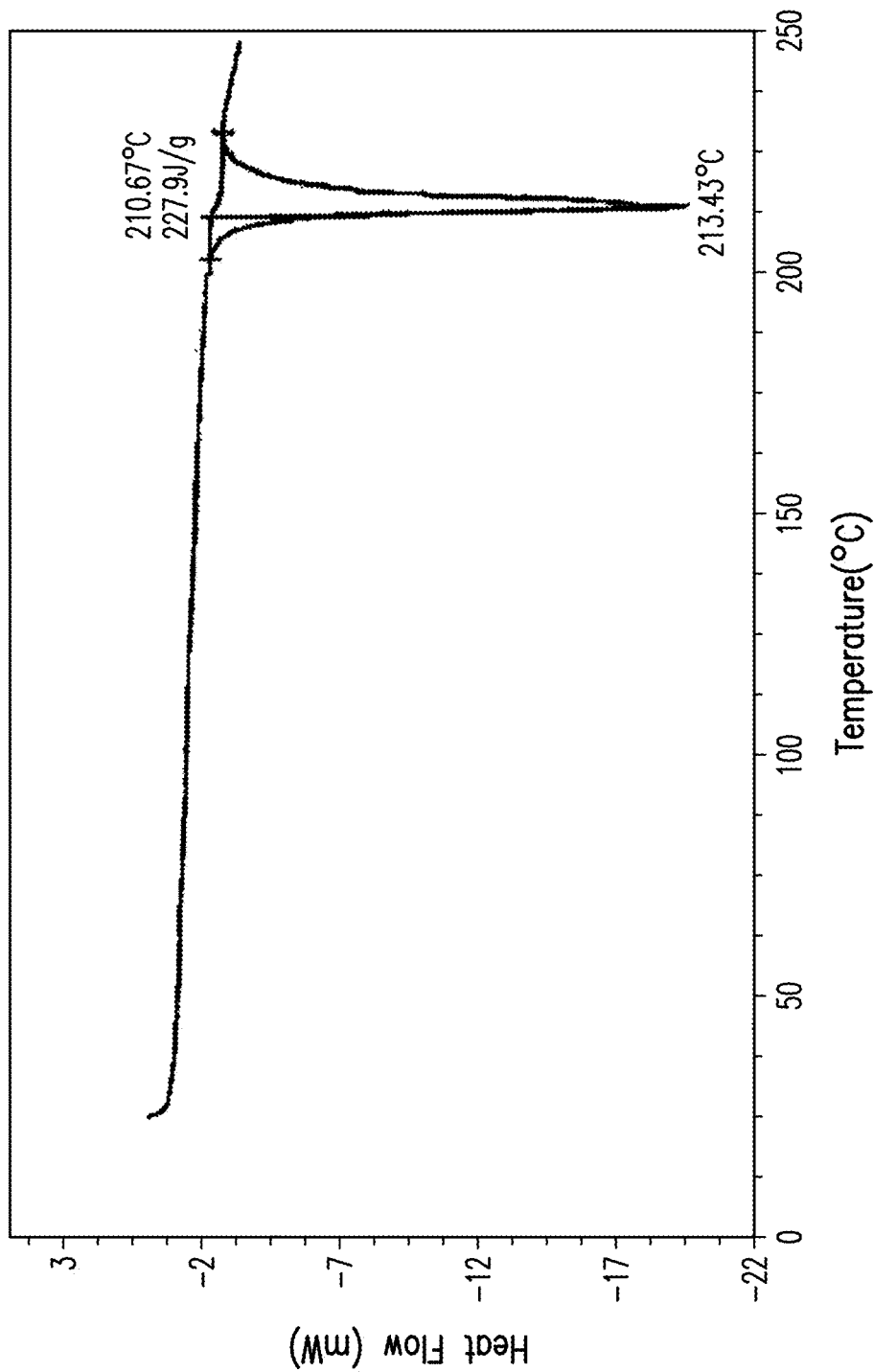
FIG. 2 is a differential scanning calorimetry (DSC) profile of compound 1 Form 3.

In another embodiment, Form 3 is characterized by the differential scanning calorimetry profile (DSC) shown in FIG. 2. The DSC graph plots the heat flow as a function of temperature from a sample, the temperature rate change being about 10° C./min. The profile is characterized by a strong endothermic transition with an onset temperature of about 210.7° C. with a melt at about 213.4° C.

Figure 3:
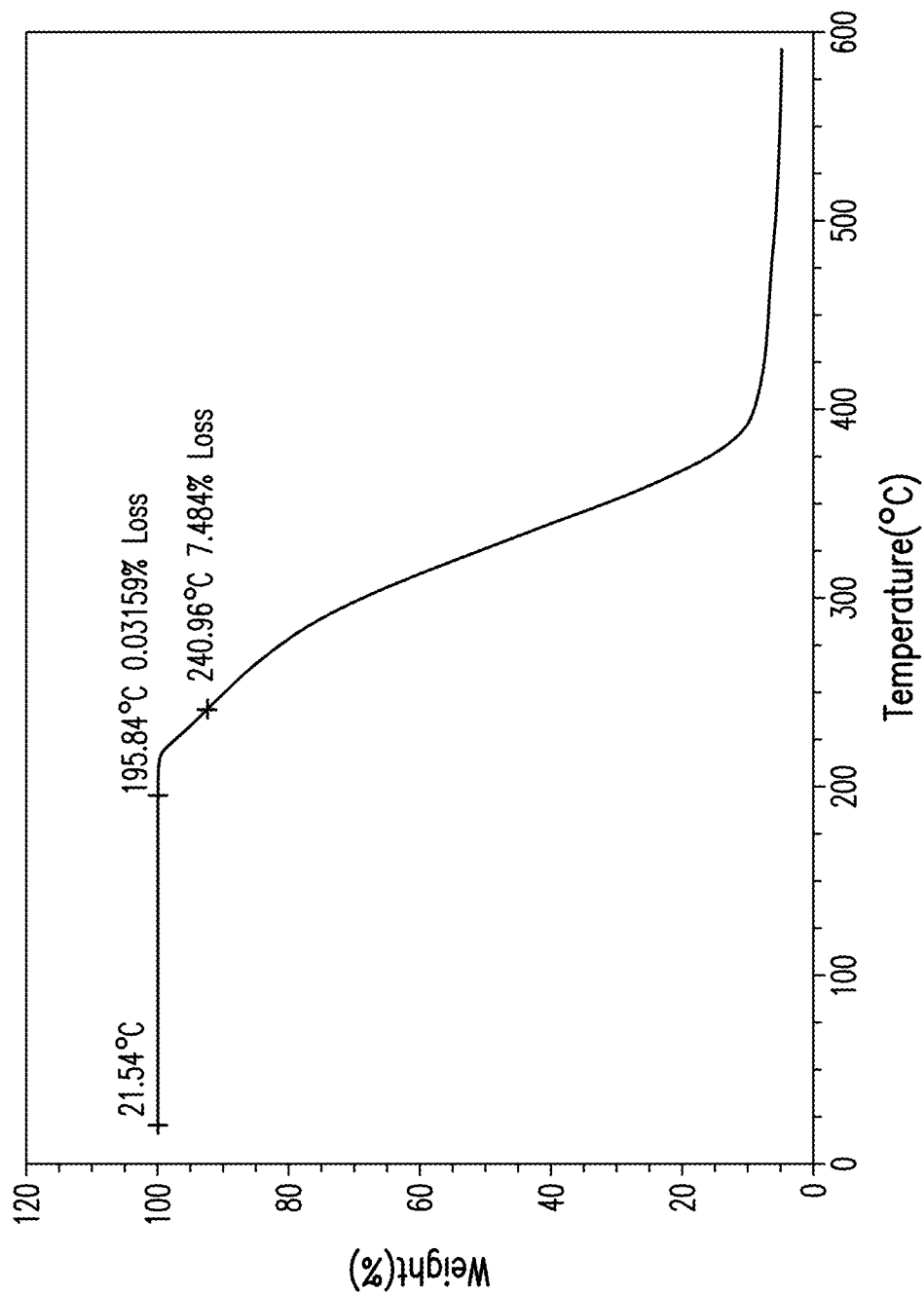
FIG. 3 is a thermal gravimetric analysis (TGA) profile of compound 1 Form 3.

In another embodiment, Form 3 is characterized by thermal gravimetric analysis (TGA) shown in FIG. 3. The TGA profile graphs the percent loss of weight of the sample as a function of temperature, the temperature rate change being about 10° C./min. The weight loss represents a loss of about 0.03% of the weight of the sample as the temperature is changed from about 21° C. to 196° C. and about 7.5% of the weight of the sample as the temperature is changed from about 196° C. to 241° C.

Figure 4:
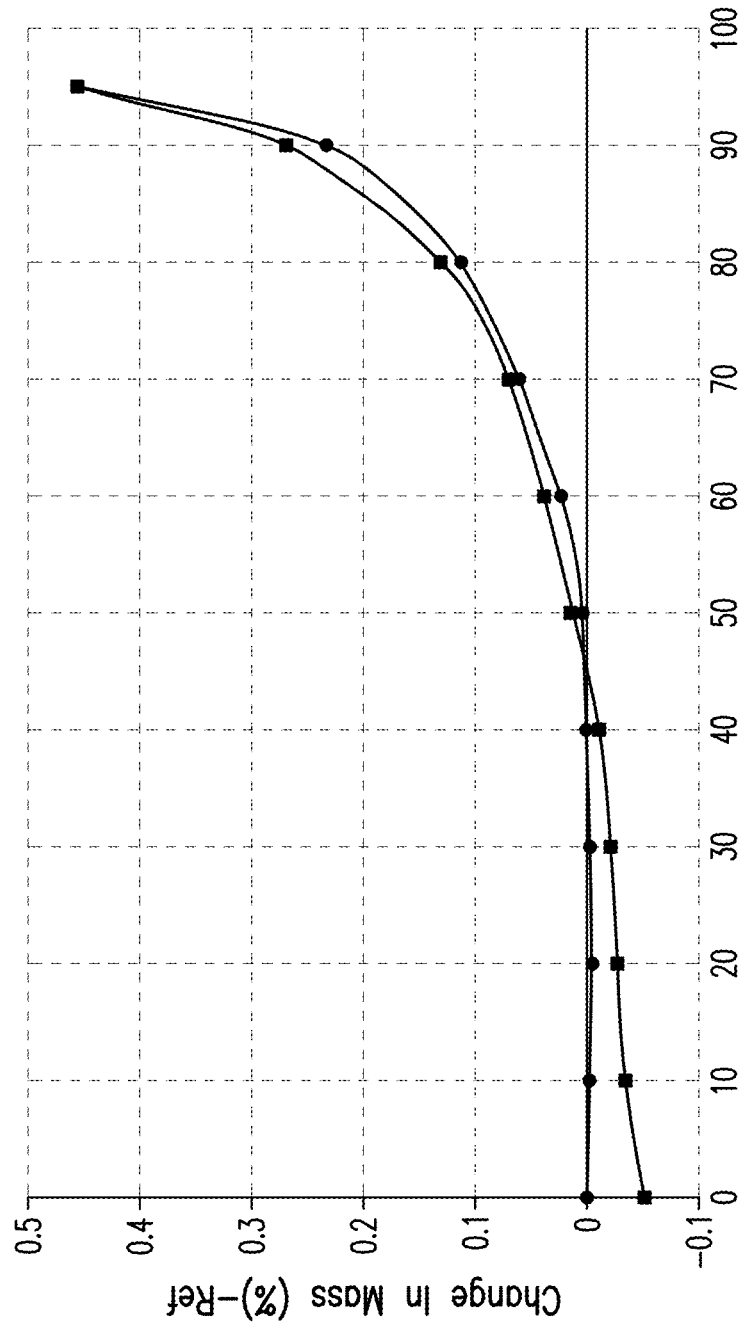
FIG. 4 is a dynamic vapor sorption (DVS) profile of compound 1 Form 3.

In another embodiment, Form 3 is characterized by an X-ray powder diffraction pattern substantially similar to FIG. 1. In another embodiment, Form 3 is characterized by a differential scanning calorimetry (DSC) profile substantially similar to FIG. 2. In another embodiment, Form 3 is characterized by a thermal gravimetric analysis (TGA) profile substantially similar to FIG. 3. In further embodiments, a single crystalline form of Form 3 is characterized by one or more of the features listed in this paragraph. In another embodiment, Form 3 is characterized by a DYS profile substantially similar to FIG. 4.

3. Intragranular Excipients

In one embodiment, the tablets provided herein comprise one or more intragranular excipients selected from the group consisting of a diluent, a binder, a solubility enhancer, disintegrant, a glidant, a lubricant, a stabilizer and a pH adjustor.

(a) Diluents

Diluents are excipients which are used for diluting formulation components such as active ingredients and adjusting them to amounts appropriate to the formulation, and in some cases, for imparting stability, improved moldability, and the like. Diluents are also referred to as fillers or bulking agents. Examples of diluents include lactose, glucose, sucrose, maltose (preferably candy powder (containing 83% or more of maltose)), trehalose, sugars such as lactose and fructose, sugar alcohols such as mannitol, xylitol, maltitol, sorbitol, and erythritol, and crystalline cellulose. In one embodiment, the diluent used in the tablets provided herein is microcrystalline cellulose PH102.

In certain embodiments, the tablet comprises a diluent in an amount of about 30 to 50% by weight based on the total weight of the tablet, such as for example 35 to 45% by weight based on the total weight of the tablet. In certain embodiments, the tablet comprises a diluent in an amount of about 34.50, 39.50, 44.50 or 45% by weight based on the total weight of the tablet.

In certain embodiments, the tablet comprises microcrystalline cellulose in an amount of about 30 to 50% by weight based on the total weight of the tablet, such as for example 35 to 45% by weight based on the total weight of the tablet. In certain embodiments, the tablet comprises microcrystalline cellulose in an amount of about 34.50, 39.50, 44.50 or 45% by weight based on the total weight of the tablet. In certain embodiments, the tablet comprises microcrystalline cellulose in an amount of about 34.5% by weight based on the total weight of the tablet. In certain embodiments, the tablet comprises microcrystalline cellulose in an amount of about 39.50% by weight based on the total weight of the tablet. In certain embodiments, the tablet comprises microcrystalline cellulose in an amount of about 44.50% by weight based on the total weight of the tablet. In certain embodiments, the tablet comprises microcrystalline cellulose in an amount of about 45% by weight based on the total weight of the tablet.

(b) Binders

Binders are classified as excipients which impart the stickiness for maintaining quality after forming the tablet. The amount of a binder in the tablets provided herein varies based on, for example, the type of binders (properties such as molecular weight, solubility, and viscosity), the type and amount of other excipients, the type and amount of the composite, and its dosage form and the formulation step (granulation method and tableting method).

Examples of binders useful in the tablets include: hydroxypropyl cellulose (product name: HPC-SSL, HPC-SL, HPC-L, METOLOSE SR, KLUCEL-EF, KLUCEL-LF, KLUCEL-JF, and the like), hypromellose (product name: TC-5E, TC-5R, TC-5M, TC-5S, METOLOSE 65SH, METHOCEL F, and the like), methyl cellulose (product name: METOLOSE SM, METHOCEL A, and the like), hydroxyethyl cellulose, hydroxyethyl methylcellulose, hydroxypropyl starch, povidone (product name: Kollidon, Plasdone, and the like), corn starch, potato starch, rice starch and gelatin.

In one embodiment, the binder is hydroxypropyl cellulose (KLUCEL™ EXF PHARM).

In certain embodiments, the amount of the binder in the tablets provided herein is about 5% by weight or less based on the total weight of the tablet. In one embodiment, the binder is about 1 to 3% by weight, in another embodiment, the binder is about 2% by weight.

In certain embodiments, the amount of hydroxypropyl cellulose in the tablets provided herein is about 5% by weight or less based on the total weight of the tablet. In one embodiment, hydroxypropyl cellulose is about 1 to 3% by weight, in another embodiment, hydroxypropyl cellulose is about 2% by weight.

c) Disintegrants

Disintegrants are excipients to improve the disintegration of a preparation, more particularly, they are excipients to be added to disintegrate a tablet by absorbing water in the body after administration, swelling, and thereby facilitating release of the active ingredient. In certain embodiments, the amount of disintegrators in the tablets provided herein is selected such that the disintegration and the dissolution of the tablet are not reduced. In certain embodiments, the amount of disintegrator in the tablet is about 10% by weight or less based on the total weight of the tablet.

Examples of the disintegrators include: sodium starch glycolate (product name: Primojel, GLYCOLYS, EXPLOTAB, and the like), sodium alginate, carmellose, carmellose calcium, and carmellose sodium, glycerin fatty acid ester, low-substituted sodium carboxymethyl starch and partially pregelatinized starch (product name: LYCATAB C, PCS, Graflow, starch 1500, and the like).

In one embodiment, the disintegrator in the tablet provided herein is sodium starch glycolate.

In one embodiment, the amount of disintegrator in the tablet is about 4-8% by weight. In one embodiment, the amount of disintegrator in the tablet is about 6% by weight based on the total weight of the tablet.

In one embodiment, the amount of sodium starch glycolate in the tablet is about 4-8% by weight. In one embodiment, the amount of sodium starch glycolate in the tablet is about 6% by weight based on the total weight of the tablet.

(d) Wetting Agents

The wetting agents are excipients to improve solubilization of the active agent. Examples of wetting agents include sodium lauryl sulfate and polyethylene-polypropylene glycol. In one embodiment, the wetting agent is sodium lauryl sulfate.

In certain embodiments, the amount of wetting agent in the tablet is about 3% by weight or less based on the total weight of the tablet. In one embodiment, the amount of the wetting agent in the tablet is about 1-2% by weight. In one embodiment, the amount of the wetting agent in the tablet is about 1% by weight based on the total weight of the tablet.

In certain embodiments, the amount of sodium lauryl sulfate in the tablet is about 3% by weight or less based on the total weight of the tablet. In one embodiment, the amount of sodium lauryl sulfate in the tablet is about 1-2% by weight. In one embodiment, the amount of sodium lauryl sulfate in the tablet is about 1% by weight based on the total weight of the tablet.

(e) Lubricants

Examples of lubricants include magnesium stearate, calcium stearate, sucrose fatty acid ester, polyethylene glycol, talc, sodium stearyl fumarate, and stearic acid. In one embodiment, the lubricant used in the tablet formulations herein is magnesium stearate.

In one embodiment, the amount of magnesium stearate in the tablet is less than 2% or less than 1% by weight based on the total weight of the tablet. In one embodiment, the amount of magnesium stearate in the tablet is about 0.75% by weight based on the total weight of the tablet.

(f) Glidants

In one embodiment, the glidant used in the tablets provided herein is colloidal silicon dioxide. In certain embodiments, the glidant in intragranular excipients is present in an amount of about 1 to 3% by weight based on the total weight of the tablet. In certain embodiments, the glidant in intragranular excipients is colloidal silicon dioxide which is present in an amount of about 0.75% by weight based on the total weight of the tablet.

(g) Other Excipients

The tablet provided herein may contain various excipients other than the above-mentioned excipients, which are pharmaceutically acceptable and used as excipients. Examples of the other excipients include, but are not limited to, solubility enhancers, stabilizers, pH adjustors, coating agents and pigments. In one embodiment, the other excipient is selected from a solubility enhancer, a stabilizer, and a pH adjustor.

The amount of these excipients in the tablets provided herein is selected such that the dissolution of Compound 1 from the tablet is not negatively affected. In one embodiment, the total amount of these excipients is about 5% or less by weight based on the total weight of the tablet or in one embodiment, the amount is 3% or less by weight or less.

In certain embodiments, the tablets comprise a stabilizer, such as hypromellose acetate succinate in an amount less than 3% by weight based on the total weight of the tablet. In one embodiment, the amount of hypromellose acetate succinate in the tablet is about 1% by weight based on the total weight of the tablet.

In certain embodiments, the tablets comprise a coating agent, such as polyvinyl alcohol.

In certain embodiments, the tablets comprise a pigment, such as titanium dioxide.

4. Extragranular Excipients

In one embodiment, the tablets provided herein comprise one or more extragranular excipients selected from the group consisting of a diluent, a disintegrant, a glidant, a lubricant, and a coating agent.

(a) Diluents

In one embodiment, the diluent used in the extragranular excipient is microcrystalline cellulose PH 102. In certain embodiments, the diluent in the extragranular excipients is present in an amount of about 5 to 50% by weight based on the total weight of the tablet. In certain embodiments, the diluent in the extragranular excipients is present in an amount of about 5 to 30% by weight based on the total weight of the tablet. In certain embodiments, the diluent in the extragranular excipients is present in an amount of about 5 to 20% by weight based on the total weight of the tablet.

In certain embodiments, the diluent in the extragranular excipients is microcrystalline cellulose which is present in an amount of about 5 or 50% by weight based on the total weight of the tablet. In certain embodiments, the diluent in the extragranular excipients is microcrystalline cellulose which is present in an amount of about 5 or 25% by weight based on the total weight of the tablet. In certain embodiments, the diluent in the extragranular excipients is microcrystalline cellulose which is present in an amount of about 10 or 25% by weight based on the total weight of the tablet. In certain embodiments, the diluent in the extragranular excipients is microcrystalline cellulose which is present in an amount of about 9.5 or 20% by weight based on the total weight of the tablet. In certain embodiments, the diluent in the extragranular excipients is microcrystalline cellulose which is present in an amount of about 10 or 20% by weight based on the total weight of the tablet. In certain embodiments, the diluent in the extragranular excipients is microcrystalline cellulose which is present in an amount of about 9.5% by weight based on the total weight of the tablet. In certain embodiments, the diluent in the extragranular excipients is microcrystalline cellulose which is present in an amount of about 14.5% by weight based on the total weight of the tablet. In certain embodiments, the diluent in the extragranular excipients is microcrystalline cellulose which is present in an amount of about 20% by weight based on the total weight of the tablet.

b) Disintegrants

In one embodiment, the disintegrant used in the extragranular excipient is sodium starch glycolate. In certain embodiments, the disintegrant in the extragranular excipients is present in an amount of about 1 to 5% by weight based on the total weight of the tablet. In certain embodiments, the disintegrant in the extragranular excipients is present in an amount of about 1 to 3% by weight based on the total weight of the tablet. In certain embodiments, the disintegrant in the extragranular excipients is sodium starch glycolate which is present in an amount of about 2% by weight based on the total weight of the tablet.

c) Glidants

In one embodiment, the glidant used in the extragranular excipient is colloidal silicon dioxide. In certain embodiments, the glidant in the extragranular excipients is present in an amount of about 1 to 3% by weight based on the total weight of the tablet. In certain embodiments, the glidant in the extragranular excipients is colloidal silicon dioxide which is present in an amount of about 0.5% by weight based on the total weight of the tablet.

d) Lubricants

In one embodiment, the lubricant used in the extragranular excipient is magnesium stearate. In certain embodiments, the lubricant in the extragranular excipients is present in an amount of about 1 to 3% by weight based on the total weight of the tablet. In certain embodiments, the lubricant in the extragranular excipients is magnesium stearate which is present in an amount of about 0.75% by weight based on the total weight of the tablet.

(f) Other Excipients

The tablet provided herein may contain various extragranular excipients other than the above-mentioned excipients, which are pharmaceutically acceptable and used as excipients. Examples of the other excipients include, but are not limited to, coloring agents, coating agents and flavoring agents.

In certain embodiments, the tablet is a coated tablet. In certain embodiments, the coating is a film coating. In certain embodiments, the coating agent is Opadry II. In certain embodiments, the coating agent comprises polyvinyl alcohol.

5. Methods of Preparation

Any conventional method for obtaining a tablet can be used, for example, the methods described in pharmacopoeias such as the U.S. Pharmacopeia, and the European Pharmacopoeia, may be used.

In certain embodiments, the method for making a tablet comprises the steps of mixing, roller compaction, final blending, compression and coating. In certain embodiments, the method provided herein is for making a coated tablet of 25-300 mg strength of Compound 1. In certain embodiments, the method provided herein is for making a coated tablet of 25 mg, 50 mg, 100 mg, 150 mg, or 200 mg strength of Compound 1.

In certain embodiments, the method provided herein is for making a coated tablet of 25-300 mg strength of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol. In certain embodiments, the method provided herein is for making a coated tablet of 25 mg, 50 mg, 100 mg, 150 mg or 200 mg strength of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol.

In one embodiment, the method for making a tablet comprises blending Compound 1 with an intragranular excipient and an extragranular excipient and compressing with a compression tooling.

In certain embodiments, the method for making a tablet comprises one or more of the following steps: 1) pre-blending, 2) lubrication, 3) dry granulation, 4) milling, 5) final blending, 6) compression and 7) film coating.

In one embodiment, the pre-blending step comprises mixing Compound 1 with intragranular components including, a diluent, a binder, a solubility enhancer, a disintegrant and a glidant to obtain a pre-blend.

In one embodiment, the pre-blend is mixed with a lubricant to obtain a lubricated pre-blend.

In one embodiment, the lubricated pre-blend is dry granulated to obtain compacted granules, which are milled.

In one embodiment, the milled granules are mixed with extra-granular excipients including a diluent, a disintegrant, a glidant, followed by a lubricant to obtain a final blend. The final blend is then compression molded to obtain a tablet. In certain embodiment, the tablet is coated with a coating agent.

Examples of the equipment used in the processes for making a tablet provided here include, roller compacters, such as Gerteis Minipactor®; blenders, such as PK Blender Drive, O'Hara Drive; smooth rollers; tabletop/floor balances; tablet presses, such as Piccola single layer tablet press; tooling such as, M340 high chromium steel, 0.25" round, chromium nitride ultra coat, 0.25" round (Natoli), standard, plain round tooling, 6 mm (EC), chromium nitride-IBED coated tooling, 0.25" round (Beamalloy); calipers; disintegration apparatus; friability testers and hardness testers.

Any tableting conditions suitable for tablet molding can be used. In certain embodiments, tableting force is used such that the tablets are not damaged during the manufacturing process. The tableting force may be, for example, from about 1 kN to about 40 kN in one embodiment, from about 3 kN to about 35 kN in another embodiment, and from about 5 kN to about 32 kN in yet another embodiment. In one embodiment, the roller force in dry granulation step is about 2 to 6 kN/cm. In one embodiment, the roller force in dry granulation step is about 3 kN/cm, 3.5 kN/cm or 5.2 kN/cm. In one embodiment, the compression force in the compression step is about 9-10 kN, 10-11 kN, 10-12 kN, 12-13 kN, 12-18 kN, 14-18 kN, 15-18 kN or 18-19 kN.

Any tablet hardness suitable for tablet molding can be used. The tablet hardness may be, for example, from about 4 kp (kilopound) to about 35 kp, or about 4 kp to about 32 kp. In one embodiment, the tablet hardness for 25 mg tablet is about 4 kp to about 10 kp. In one embodiment, the tablet hardness for 150 mg tablet is about 12 kp to about 20 kp.

Any tablet thickness suitable for tablet molding can be used. The tablet thickness may be, for example, from about 1.5 mm to about 7 mm. In one embodiment, the tablet thickness for 25 mg tablet is about 2 mm to about 4 mm. In one embodiment, the tablet thickness for 150 mg tablet is about 4 mm to about 6 mm.

Figure 7:
FIG. 7 illustrates loss of tablet residue due to sticking and punch filming using methods known in the art.
Figure 8:
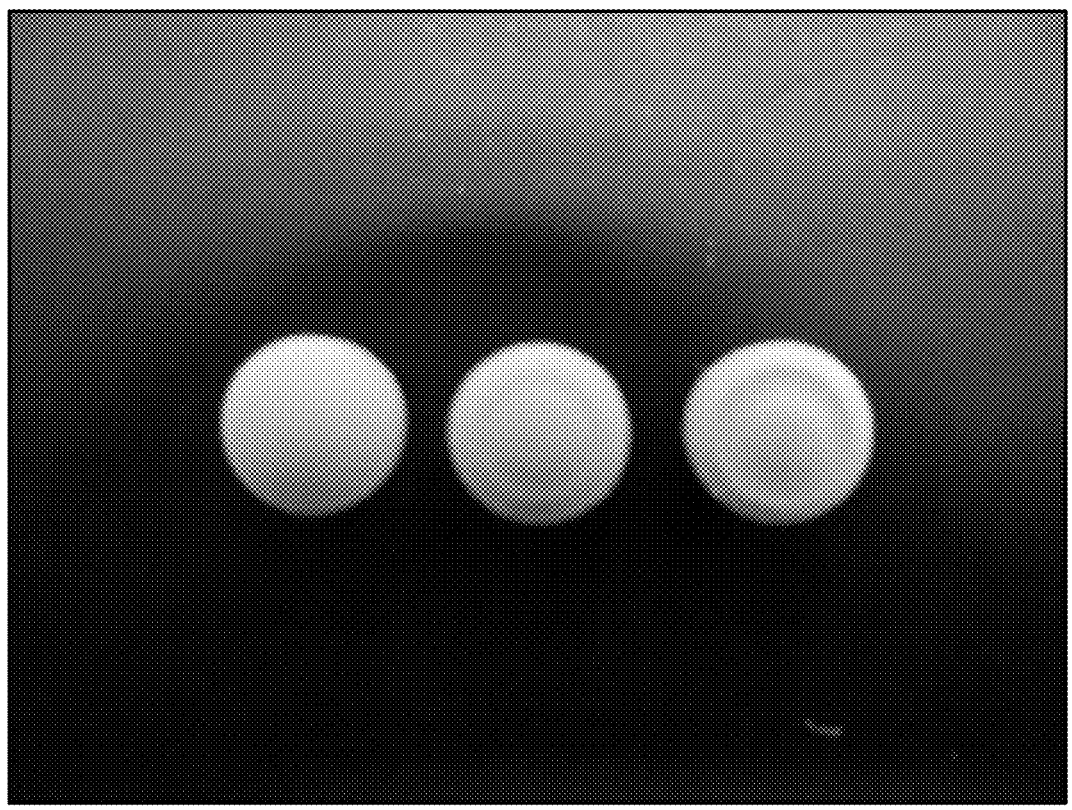
FIG. 8 illustrates loss of crown in round tablets prepared by methods known in the art.
Figure 9:
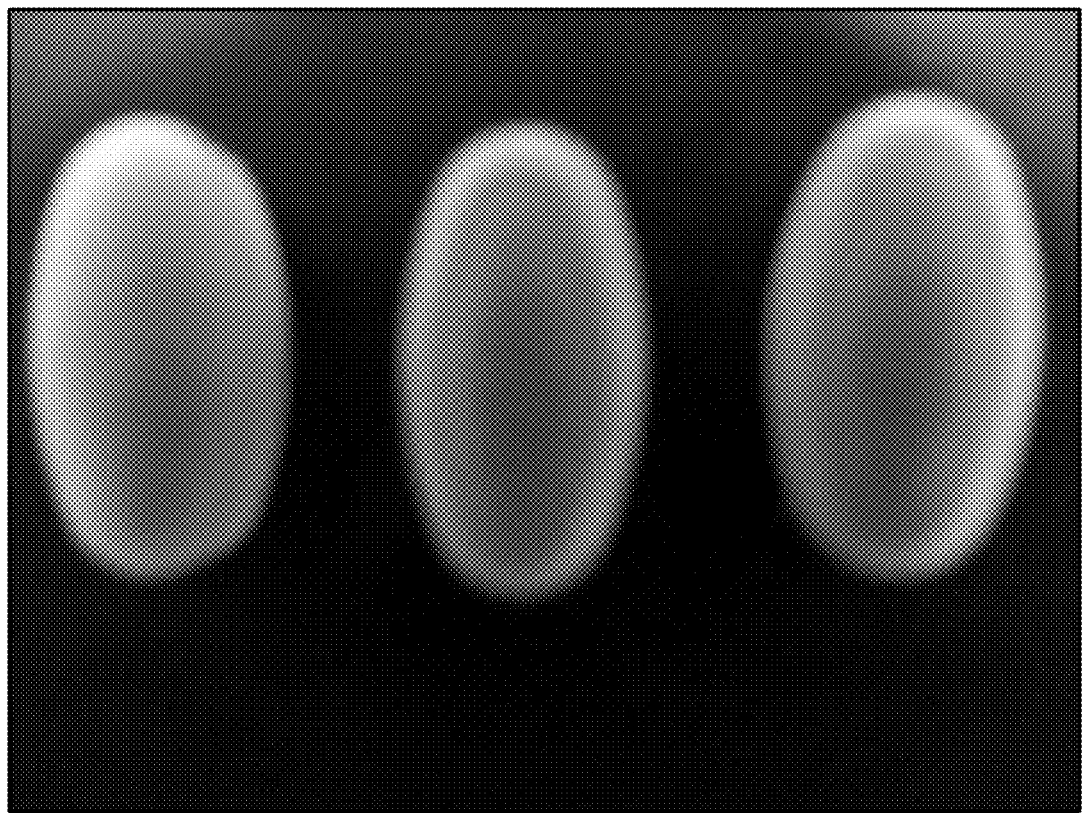
FIG. 9 illustrates loss of crown in oval tablets prepared by methods known in the art.

In certain embodiments, the tablet compositions provided herein reduce or eliminate sticking and/or punch filming issues during the tablet formation. FIG. 7 illustrates loss of tablet residue after 5 to 10 minutes of tablet manufacture due to sticking and punch filming in methods known in the art. FIG. 8 illustrates loss of crown in round tablets prepared by methods known in the art. FIG. 9 illustrates loss of crown in oval tablets prepared by methods known in the art.

In certain embodiments, the tablet compositions provided herein reduce or eliminate the loss of material from the tablet surface due to sticking and/or punch filming during formation of the tablets comprising Compound 1.

When the tablet is coated, conventional methods may be used for coating the tablet. Examples of the coating methods include pan coating and dip coating. Coating agents may be appropriately added alone or in a combination of two or more in appropriate quantities. The coating level is not limited, so long as a film may be formed on the tablet. The coating level is, for example, from 1% by weight to 5% by weight of the tablet weight. The coated tablet may be dried after the coating, and any pharmaceutically acceptable drying method may be used. Any pharmaceutically acceptable coating agent may be used. Examples of coating agents include product names: Opadry and Opadry II.

The tablets provided herein exhibit rapid dispersion and dissolution. In one embodiment, in the tablets provided herein, more than 75% of Compound 1 dissolves within 15-60 minutes. In one embodiment, in the tablets provided herein, more than 80% of Compound 1 dissolves within 15-60 minutes. In one embodiment, in the tablets provided herein, more than 85% of Compound 1 dissolves within 15-60 minutes. In one embodiment, in the tablets provided herein, more than 90% of Compound 1 dissolves within 15-60 minutes. In one embodiment, in the tablets provided herein, more than 95% of Compound 1 dissolves within 15-60 minutes. In certain embodiments, the dissolution rate after 15 minutes from the beginning of the dissolution test is 60% or more, 70% or more, 80% or more or 90% or more. In certain embodiments, the dissolution rate after 30 minutes from the beginning of the dissolution test is 60% or more, 70% or more, 80% or more or 90% or more. In certain embodiments, the dissolution rate after 45 minutes from the beginning of the dissolution test is 60% or more, 70% or more, 80% or more or 90% or more. In certain embodiments, the dissolution rate after 60 minutes from the beginning of the dissolution test is 60% or more, 70% or more, 80% or more or 90% or more.

The tablet provided herein has a good stability during storage. In one embodiment, dissolution of the tablet is not reduced for up to 1-4 weeks under accelerated stability studies. In certain embodiments, the accelerated stability studies encompass storing at temperatures from 40-75° C. at relative humidity of 75%. In one embodiment, dissolution of the tablet is not reduced for up to at least 1 month, at least 2 months, at least 3 months, at least 4 months, at least 6 months, at least 8 months, at least 10 months, or at least 12 months, in a conventional packaging.

In one embodiment, the tablet composition provided herein comprises amorphous 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol and/or 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate. In one embodiment, the amorphous content in the tablet composition at the time of manufacture of the tablet is ≤10%.

In one embodiment, the tablet formulations provided herein show none to minor increase in the amorphous content (amorphous 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol and amorphous 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate) upon storage.

6. Exemplary Tablet Formulations

Examples of the tablets provided herein having the desired stability during storage include a tablet comprising about 20-30% Compound 1; intra-granular excipients comprising about 30-45% microcrystalline cellulose, about 2% hydroxypropyl cellulose, about 6% sodium starch glycolate, about 1% sodium lauryl sulfate, about 1% hypromellose acetate succinate, about 1.5% colloidal silicon dioxide, and about 0.75% magnesium stearate; and extra-granular excipients comprising about 5-50% microcrystalline cellulose, about 2% sodium starch glycolate, about 0.5% colloidal silicon dioxide, and about 0.75% magnesium stearate, all based on total weight of the tablet. In one embodiment, Compound 1 is 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate. In one embodiment, Compound 1 is polymorph Form 3 of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate.

Examples of the tablets provided herein having the desired stability during storage include a tablet comprising about 20-30% Compound 1; intra-granular excipients comprising about 30-45% microcrystalline cellulose, about 2% hydroxypropyl cellulose, about 6% sodium starch glycolate, about 1% sodium lauryl sulfate, about 1% hypromellose acetate succinate, about 1.5% colloidal silicon dioxide, and about 0.75% magnesium stearate; and extra-granular excipients comprising about 9-25% microcrystalline cellulose, about 2% sodium starch glycolate, about 0.5% colloidal silicon dioxide, and about 0.75% magnesium stearate, all based on total weight of the tablet. In one embodiment, Compound 1 is 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate. In one embodiment, Compound 1 is polymorph Form 3 of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate.

In one embodiment, the tablet comprises Compound 1 in an amount from about 20% to about 30%, an intragranular excipient selected from about 34.5%, 44.5% and to about 39.5% microcrystalline cellulose, about 2% hydroxypropyl cellulose by and 6%, sodium starch glycolate, and an extragranular excipient selected from about 20% microcrystalline cellulose and about 2%, sodium starch glycolate by weight based on total weight of the tablet. In one embodiment, Compound 1 is 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate. In one embodiment, Compound 1 is polymorph Form 3 of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate.

In one embodiment, the tablet comprises about 30% Compound 1; intra-granular excipients comprising about 45% microcrystalline cellulose, about 2% hydroxypropyl cellulose, about 6% sodium starch glycolate, about 1% sodium lauryl sulfate, about 1% hypromellose acetate succinate, about 1.5% colloidal silicon dioxide, and about 0.75% magnesium stearate; and extra-granular excipients comprising about 9.5% microcrystalline cellulose, about 2% sodium starch glycolate, about 0.5% colloidal silicon dioxide, and about 0.75% magnesium stearate. In one embodiment, Compound 1 is 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate. In one embodiment, Compound 1 is polymorph Form 3 of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate.

In one embodiment, the tablet comprises about 30% Compound 1; intra-granular excipients comprising about 34.50% microcrystalline cellulose, about 2% hydroxypropyl cellulose, about 6% sodium starch glycolate, about 1% sodium lauryl sulfate, about 1% hypromellose acetate succinate, about 1.5% colloidal silicon dioxide, and about 0.75% magnesium stearate; and extra-granular excipients comprising about 20% microcrystalline cellulose, about 2% sodium starch glycolate, about 0.5% colloidal silicon dioxide, and about 0.75% magnesium stearate. In one embodiment, Compound 1 is 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate. In one embodiment, Compound 1 is polymorph Form 3 of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate.

In one embodiment, the tablet comprises about 20% Compound 1; intra-granular excipients comprising about 44.50% microcrystalline cellulose, about 2% hydroxypropyl cellulose, about 6% sodium starch glycolate, about 1% sodium lauryl sulfate, about 1% hypromellose acetate succinate, about 1.5% colloidal silicon dioxide, and about 0.75% magnesium stearate; and extra-granular excipients comprising about 20% microcrystalline cellulose, about 2% sodium starch glycolate, about 0.5% colloidal silicon dioxide, and about 0.75% magnesium stearate. In one embodiment, Compound 1 is 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate. In one embodiment, Compound 1 is polymorph Form 3 of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate.

In one embodiment, the tablet comprises about 25% Compound 1; intra-granular excipients comprising about 39.50% microcrystalline cellulose, about 2% hydroxypropyl cellulose, about 6% sodium starch glycolate, about 1% sodium lauryl sulfate, about 1% hypromellose acetate succinate, about 1.5% colloidal silicon dioxide, and about 0.75% magnesium stearate; and extra-granular excipients comprising about 20% microcrystalline cellulose, about 2% sodium starch glycolate, about 0.5% colloidal silicon dioxide, and about 0.75% magnesium stearate. In one embodiment, Compound 1 is 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate. In one embodiment, Compound 1 is polymorph Form 3 of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate.

In certain embodiments, the tablets provided herein comprise Compound 1, colloidal silicon dioxide, hydroxypropyl cellulose, hypromellose acetate succinate, iron oxide yellow, magnesium stearate, microcrystalline cellulose, polyethylene glycol, polyvinyl alcohol, sodium lauryl sulfate, sodium starch glycolate, talc, and titanium dioxide. In one embodiment, Compound 1 is 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate. In one embodiment, Compound 1 is polymorph Form 3 of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate.

7. Methods of Use

The tablet formulations provided herein are useful for treating a cancer selected from glioma, melanoma, chondrosarcoma, cholangiocarcinoma (e.g., glioma), angioimmunoblastic T-cell lymphoma (AITL), acute myelogenous leukemia (AML), myelodysplastic syndrome (MDS), chronic myelomonocytic leukemia (CMML), lymphoma (e.g., T-cell lymphoma)) or myeloproliferative neoplasm (MPN), lessen the severity of the disease/disorder (i.e., a cancer selected from glioma, melanoma, chondrosarcoma, cholangiocarcinoma (e.g., glioma), angioimmunoblastic T-cell lymphoma (AITL), acute myelogenous leukemia (AML), myelodysplastic syndrome (MDS), chronic myelomonocytic leukemia (CMML), lymphoma (e.g., T-cell lymphoma) or myeloproliferative neoplasm (MPN), each characterized by the presence of a mutant allele of IDH2.

In one embodiment, provided herein is a method of treating and preventing a disease or condition, comprising the administration of a tablet composition comprising Compound 1, wherein the disease is a cancer selected from glioma, melanoma, chondrosarcoma, cholangiocarcinoma (e.g., glioma), angioimmunoblastic T-cell lymphoma (AITL), acute myelogenous leukemia (AML), myelodysplastic syndrome (MDS), chronic myelomonocytic leukemia (CMML), or lymphoma (e.g., T-cell lymphoma)), lessen the severity of the disease/disorder (i.e., a cancer selected from glioma, melanoma, chondrosarcoma, cholangiocarcinoma (e.g., glioma), angioimmunoblastic T-cell lymphoma (AITL), acute myelogenous leukemia (AML), myelodysplastic syndrome (MDS), chronic myelomonocytic leukemia (CMML), or lymphoma (e.g., T-cell lymphoma), each characterized by the presence of a mutant allele of IDH2.

In one embodiment, provided herein is a method of treating AML selected from newly diagnosed AML, previously untreated AML, AML arising from myelodysplastic syndrome (MDS), AML arising from antecedent hematologic disorder (AHD) and AML arising after exposure to genotoxic injury. In certain embodiments, the genotoxic injury is resulting from radiation and/or chemotherapy. In one embodiment, provided herein is a method of treating AML arising after exposure to genotoxic injury resulting from radiation and/or chemotherapy), each characterized by the presence of a mutant allele of IDH2.

In one embodiment, provided herein is a method of treating newly diagnosed AML characterized by the presence of a mutant allele of IDH2.

In one embodiment, provided herein is a method of treating previously untreated AML characterized by the presence of a mutant allele of IDH2.

In one embodiment, provided herein is a method of treating AML arising from myelodysplastic syndrome (MDS) characterized by the presence of a mutant allele of IDH2.

In one embodiment, provided herein is a method of treating AML arising from antecedent hematologic disorder (AHD) characterized by the presence of a mutant allele of IDH2.

In one embodiment, provided herein is a method of treating AML arising after exposure to genotoxic injury characterized by the presence of a mutant allele of IDH2.

In one embodiment, provided herein is a method of treating myeloproliferative neoplasm (MPN).

In one aspect of this embodiment, the mutant IDH2 has an R140X mutation. In another aspect of this embodiment, the R140X mutation is a R140Q mutation. In another aspect of this embodiment, the R140X mutation is a R140W mutation. In another aspect of this embodiment, the R140X mutation is a R140L mutation. In another aspect of this embodiment, the mutant IDH2 has an R172X mutation. In another aspect of this embodiment, the R172X mutation is a R172K mutation. In another aspect of this embodiment, the R172X mutation is a R172G mutation. A cancer selected from acute myelogenous leukemia (AML), myelodysplastic syndrome (MDS), chronic myelomonocytic leukemia (CMML), or lymphoma (e.g., T-cell lymphoma) can be analyzed by sequencing cell samples to determine the presence and specific nature of (e.g., the changed amino acid present at) a mutation at amino acid 140 and/or 172 of IDH2.

Without being bound by theory, applicants believe that mutant alleles of IDH2 wherein the IDH2 mutation results in a new ability of the enzyme to catalyze the NADPH-dependent reduction of α-ketoglutarate to R(−)-2-hydroxy-glutarate, and in particular R140Q and/or R172K mutations of IDH2, characterize a subset of all types of cancers described herein, without regard to their cellular nature or location in the body. Thus, the methods of one aspect are useful to treat a hematologic cancer selected from acute myelogenous leukemia (AML), myelodysplastic syndrome (MDS), chronic myelomonocytic leukemia (CMML), or lymphoma (e.g., T-cell lymphoma) or solid tumor selected from glioma, melanoma, chondrosarcoma, cholangiocarcinoma (e.g., glioma) and angioimmunoblastic T-cell lymphoma (AITL), that is characterized by the presence of a mutant allele of IDH2 imparting such activity and in particular an IDH2 R140Q and/or R172K mutation.

In one embodiment, the efficacy of treatment is monitored by measuring the levels of 2HG in the subject. Typically levels of 2HG are measured prior to treatment, wherein an elevated level is indicated for the use of Compound 1 to treat the cancer selected from glioma, melanoma, chondrosarcoma, cholangiocarcinoma (e.g., glioma), angioimmunoblastic T-cell lymphoma (AITL), acute myelogenous leukemia (AML), myelodysplastic syndrome (MDS), chronic myelomonocytic leukemia (CMML), and lymphoma (e.g., T-cell lymphoma). Once the elevated levels are established, the level of 2HG is determined during the course of and/or following termination of treatment to establish efficacy. In certain embodiments, the level of 2HG is only determined during the course of and/or following termination of treatment. A reduction of 2HG levels during the course of treatment and following treatment is indicative of efficacy. Similarly, a determination that 2HG levels are not elevated during the course of or following treatment is also indicative of efficacy. Typically, the these 2HG measurements will be utilized together with other well-known determinations of efficacy of cancer treatment, such as reduction in number and size of tumors and/or other cancer-associated lesions, improvement in the general health of the subject, and alterations in other biomarkers that are associated with cancer treatment efficacy.

2HG can be detected in a sample by the methods of PCT Publication No. WO 2013/102431 and US Publication No. US 2013/0190287 hereby incorporated by reference in their entirety, or by analogous methods.

In one embodiment 2HG is directly evaluated.

In another embodiment a derivative of 2HG formed in process of performing the analytic method is evaluated. By way of example such a derivative can be a derivative formed in MS analysis. Derivatives can include a salt adduct, e.g., a Na adduct, a hydration variant, or a hydration variant which is also a salt adduct, e.g., a Na adduct, e.g., as formed in MS analysis.

In another embodiment a metabolic derivative of 2HG is evaluated. Examples include species that build up or are elevated, or reduced, as a result of the presence of 2HG, such as glutarate or glutamate that will be correlated to 2HG, e.g., R-2HG.

Exemplary 2HG derivatives include dehydrated derivatives such as the compounds provided below or a salt adduct thereof:

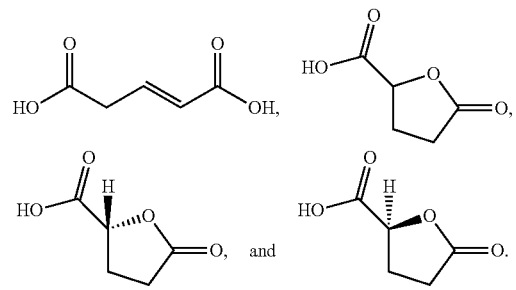

In one embodiment the cancer selected from glioma, melanoma, chondrosarcoma, cholangiocarcinoma (e.g., glioma), angioimmunoblastic T-cell lymphoma (AITL), acute myelogenous leukemia (AML), myelodysplastic syndrome (MDS), chronic myelomonocytic leukemia (CMML), and lymphoma (e.g., T-cell lymphoma) is a tumor wherein at least 30, 40, 50, 60, 70, 80 or 90% of the tumor cells carry an IDH2 mutation, and in particular an IDH2 R140Q, R140W, or R140L and/or R172K or R172G mutation, at the time of diagnosis or treatment.

In one embodiment, the cancer to be treated is AML. In some embodiments, the AML is relapsed and/or primary refractory. In some embodiments, the AML is relapsed and/or refractory. In other embodiments, the AML is previously untreated. In one embodiment, the AML is newly diagnosed AML.

In another embodiment, the cancer to be treated is MDS with refractory anemia with excess blasts (subtype RAEB-1 or RAEB-2). In other embodiments, the MDS is previously untreated. In one embodiment, the MDS is newly diagnosed MDS.

In another embodiment, the cancer to be treated is relapsed and/or primary refractory CMML.

In certain embodiments, the tablet compositions provided herein are for treating a hematologic malignancy characterized by the presence of a mutant allele of IDH2 and the absence of a FLT3 mutation and/or NRAS mutation. Exemplary methods are described in US 2017/0157132 and U.S. application Ser. No. 15/368,405, the disclosure of each of which is incorporated herein by reference in its entirety.

In one embodiment, the tablet compositions provided herein are for treating a hematologic malignancy characterized by the presence of a mutant allele of IDH2 and the absence of a FLT3 mutation. In one embodiment, the hematologic malignancy is an advanced hematologic malignancy.

In one embodiment, the hematologic malignancy is AML. In some embodiments, the AML is relapsed and/or refractory.

In one embodiment, provided herein are methods of treating a hematologic malignancy by administering a tablet composition comprising Compound 1 in combination with a therapeutically effective amount of one or more compounds that target a FLT3 pathway, wherein the hematologic malignancy is characterized by the presence of a mutant allele of IDH2 and a mutant FLT3, for example FLT3-ITD or FLT3-KDM. In one embodiment, the hematologic malignancy is an advanced hematologic malignancy. In one embodiment, the hematologic malignancy is AML. In some embodiments, the AML is relapsed and/or refractory.

In one embodiment, provided herein is a method of treating hematologic malignancies, such as acute myelogenous leukemia (AML), myelodysplastic syndrome (MDS), chronic myelomonocytic leukemia (CMML), myeloid sarcoma, multiple myeloma, lymphoma (e.g., T-cell lymphoma or B-cell lymphoma), angioimmunoblastic T-cell lymphoma (AITL) or blastic plasmacytoid dendritic cell neoplasm, each characterized by the presence of a mutant allele of IDH2 and the absence of a FLT3 mutation, comprising administering a tablet composition comprising Compound 1. In one embodiment, the hematologic malignancy is an advanced hematologic malignancy. In one embodiment, the hematologic malignancy is AML. In some embodiments, the AML is relapsed and/or refractory.

In one embodiment, provided herein is a method of treating hematologic malignancies, such as acute myelogenous leukemia (AML), myelodysplastic syndrome (MDS), chronic myelomonocytic leukemia (CMML), myeloid sarcoma, multiple myeloma, lymphoma (e.g., T-cell lymphoma or B-cell lymphoma), angioimmunoblastic T-cell lymphoma (AITL) or blastic plasmacytoid dendritic cell neoplasm, each characterized by the presence of a mutant allele of IDH2 and a mutant FLT3, for example FLT3-ITD, comprising administering a tablet composition comprising Compound 1 in combination with a therapeutically effective amount of one or more compounds that target a FLT3 pathway. Exemplary FLT3 inhibitors are described elsewhere herein. In one embodiment, the hematologic malignancy is an advanced hematologic malignancy. In one embodiment, the hematologic malignancy is AML. In some embodiments, the AML is relapsed and/or refractory.

In one embodiment, provided herein are methods of treating solid tumors by administering a tablet composition comprising Compound 1, wherein the solid tumor is characterized by the presence of a mutant allele of IDH2 and the absence of a FLT3 mutation. In one embodiment, the solid tumor is an advanced solid tumor. In some embodiments, the AML is relapsed and/or refractory.

In one embodiment, provided herein are methods of treating solid tumors by administering to a subject a tablet composition comprising Compound 1 in combination with a therapeutically effective amount of one or more compounds that target a FLT3 pathway, wherein the solid tumor is characterized by the presence of a mutant IDH2 and a mutant FLT3, for example FLT3-ITD. In one embodiment, the solid tumor is an advanced solid tumor.

In one embodiment, provided herein is a method of treating solid tumors, such as glioma, melanoma, chondrosarcoma, or cholangiocarcinoma (e.g., glioma), or treating angioimmunoblastic T-cell lymphoma (AITL), each characterized by the presence of a mutant allele of IDH2 and the absence of a FLT3 mutation, comprising administering to a subject a tablet composition provided herein.

In one embodiment, provided herein is a method of treating solid tumors, such as glioma, melanoma, chondrosarcoma, or cholangiocarcinoma (e.g., glioma), or treating angioimmunoblastic T-cell lymphoma (AITL), each characterized by the presence of a mutant allele of IDH2 and a mutant FLT3, in a subject comprising administering a tablet composition comprising Compound 1 in combination with a therapeutically effective amount of one or more compounds that target a FLT3 pathway. Exemplary FLT3 inhibitors are described elsewhere herein.

In one embodiment, provided herein is a method of treating a hematologic malignancy by administering a tablet composition comprising Compound 1, wherein the hematologic malignancy is characterized by the presence of a mutant allele of IDH2 and the absence of an NRAS mutation. In one embodiment, the hematologic malignancy is an advanced hematologic malignancy.

In one embodiment, provided herein is a method of treating a hematologic malignancy by administering a tablet composition comprising Compound 1 in combination with a therapeutically effective amount of one or more compounds that target RAS pathways, wherein the hematologic malignancy is characterized by the presence of a mutant allele of IDH2 and a mutant NRAS. In one embodiment, the hematologic malignancy is an advanced hematologic malignancy.

In one embodiment, provided herein is a method of treating a hematologic malignancy, such as acute myelogenous leukemia (AML), myelodysplastic syndrome (MDS), chronic myelomonocytic leukemia (CMML), myeloid sarcoma, multiple myeloma, lymphoma (e.g., T-cell lymphoma or B-cell lymphoma), angioimmunoblastic T-cell lymphoma (AITL) or blastic plasmacytoid dendritic cell neoplasm, each characterized by the presence of a mutant allele of IDH2 and the absence of an NRAS mutation, comprising administering a tablet composition comprising Compound 1. In one embodiment, the hematologic malignancy is an advanced hematologic malignancy.

In one embodiment, provided herein is a method of treating hematologic malignancies, such as acute myelogenous leukemia (AML), myelodysplastic syndrome (MDS), chronic myelomonocytic leukemia (CMML), myeloid sarcoma, multiple myeloma, lymphoma (e.g., T-cell lymphoma or B-cell lymphoma), angioimmunoblastic T-cell lymphoma (AITL) or blastic plasmacytoid dendritic cell neoplasm, each characterized by the presence of a mutant allele of IDH2 and a mutant NRAS comprising administering a tablet composition comprising Compound 1 in combination with a therapeutically effective amount of one or more compounds that target RAS pathways. In one embodiment, a tablet composition comprising Compound 1 is administered to the subject in combination with a therapeutically effective amount of a MEK kinase inhibitor. Exemplary MEK kinase inhibitors are described elsewhere herein. In one embodiment, the hematologic malignancy is an advanced hematologic malignancy.

In one embodiment, provided herein are methods of treating solid tumors by administering a tablet composition comprising Compound 1, wherein the solid tumor is characterized by the presence of a mutant allele of IDH2 and the absence of an NRAS mutation. In one embodiment, the solid tumor is an advanced solid tumor.

In one embodiment, provided herein are methods of treating solid tumors by administering a tablet composition comprising Compound 1 in combination with a therapeutically effective amount of one or more compounds that target RAS pathways, wherein the solid tumor is characterized by the presence of a mutant IDH2 and a mutant NRAS. In one embodiment, the solid tumor is an advanced solid tumor.

In one embodiment, provided herein is a method of treating solid tumors, such as glioma, melanoma, chondrosarcoma, or cholangiocarcinoma (e.g., glioma), or treating angioimmunoblastic T-cell lymphoma (AITL), each characterized by the presence of a mutant allele of IDH2 and the absence of an NRAS mutation, comprising administering a tablet composition comprising Compound 1.

In one embodiment, provided herein is a method of treating solid tumors, such as glioma, melanoma, chondrosarcoma, or cholangiocarcinoma (e.g., glioma), or treating angioimmunoblastic T-cell lymphoma (AITL), each characterized by the presence of a mutant allele of IDH2 and a mutant NRAS, comprising administering a tablet composition comprising Compound 1 in combination with a therapeutically effective amount of one or more compounds that target RAS pathways.

In one embodiment, provided herein are methods of treating MPN in a subject comprising administering to the subject a tablet composition comprising Compound 1 in combination with a therapeutically effective amount of a JAK2 inhibitor, wherein the subject harbors a mutant allele of IDH2 and a mutant allele of JAK2. Exemplary JAK2 inhibitors are described elsewhere herein.

In certain embodiments, provided herein is a method of treating a high risk MPN in a subject comprising administering to the subject a tablet composition comprising Compound 1 in combination with a therapeutically effective amount of a JAK2 inhibitor, wherein the subject harbors a mutant allele of IDH2 and a mutant allele of JAK2.

In one embodiment, provided herein are methods of treating AML in a subject comprising administering to the subject a tablet composition comprising Compound 1 in combination with a therapeutically effective amount of a JAK2 inhibitor, wherein the subject harbors a mutant allele of IDH2 and a mutant allele of JAK2. In some embodiments, the AML is relapsed and/or refractory.

In certain embodiments, the mutant allele of IDH2 is mIDH2-R140 or mIDH2-R172.

In certain embodiments, the mutant allele of IDH2 is mIDH2-R140Q, mIDH2-R140W, mIDH2-R140L, mIDH2-R172K, or mIDH2-R172G.

In certain embodiments, the mutant allele of JAK2 is mJAK2-V617F.

In one embodiment, prior to and/or after treatment with a composition provided herein, the method further comprises the step of evaluating the growth, size, weight, invasiveness, stage and/or other phenotype of the cancer selected from glioma, melanoma, chondrosarcoma, cholangiocarcinoma (e.g., glioma), angioimmunoblastic T-cell lymphoma (AITL), acute myelogenous leukemia (AML), myelodysplastic syndrome (MDS), chronic myelomonocytic leukemia (CMML), lymphoma (e.g., T-cell lymphoma) or MPN.

In one embodiment, prior to and/or after treatment with a composition provided herein, the method further comprises the step of evaluating the IDH2 genotype of the cancer selected from glioma, melanoma, chondrosarcoma, cholangiocarcinoma (e.g., glioma), angioimmunoblastic T-cell lymphoma (AITL), acute myelogenous leukemia (AML), myelodysplastic syndrome (MDS), chronic myelomonocytic leukemia (CMML), lymphoma (e.g., T-cell lymphoma) or MPN. This may be achieved by ordinary methods in the art, such as DNA sequencing, immuno analysis, and/or evaluation of the presence, distribution or level of 2HG.

In one embodiment, prior to and/or after treatment with a composition provided herein, the method further comprises the step of determining the 2HG level in the subject. This may be achieved by spectroscopic analysis, e.g., magnetic resonance-based analysis, e.g., MRI and/or MRS measurement, sample analysis of bodily fluid, such as blood, plasma, urine, or spinal cord fluid analysis, or by analysis of surgical material, e.g., by mass-spectroscopy (e.g. LC-MS, GC-MS).

In one embodiment Compound 1 or the tablet composition comprising Compound 1 is for use in any of the above described methods.

8. Combination Therapy

In certain embodiments, the tablet compositions provided herein are used with an additional cancer therapeutic agent or an additional cancer treatment. Exemplary additional cancer therapeutic agents and additional cancer treatments are described in US 2013/0190287, US 2017/0157132, WO 2017/066611, WO 2017/066599 and U.S. application Ser. No. 15/368,405, the disclosures of each of which is incorporated herein by reference in their entireties.

In certain embodiments, additional cancer therapeutic agents include for example, chemotherapy, targeted therapy, antibody therapies, immunotherapy, and hormonal therapy. In certain embodiments, additional cancer treatments include, for example: surgery, and radiation therapy. Examples of each of these treatments are provided below.

In some embodiments, the additional cancer therapeutic agent is a chemotherapy agent. Examples of chemotherapeutic agents used in cancer therapy include, for example, antimetabolites (e.g., folic acid, purine, and pyrimidine derivatives), alkylating agents (e.g., nitrogen mustards, nitrosoureas, platinum, alkyl sulfonates, hydrazines, triazenes, aziridines, spindle poison, cytotoxic agents, topoisomerase inhibitors and others), and hypomethylating agents (e.g., decitabine (5-aza-deoxycytidine), zebularine, isothiocyanates, azacitidine (5-azacytidine), 5-flouro-2'-deoxycytidine, 5,6-dihydro-5-azacytidine and others). Exemplary agents include Aclarubicin, Actinomycin, Alitretinoin, Altretamine, Aminopterin, Aminolevulinic acid, Amrubicin, Amsacrine, Anagrelide, Arsenic trioxide, Asparaginase, Atrasentan, Belotecan, Bexarotene, bendamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Strataplatin, Streptozocin, Talaporfin, Tegafur uracil, Temoporfin, Temozolomide, Teniposide, Tesetaxel, Testolactone, Tetranitrate, Thiotepa, Tiazofurine, Tioguanine, Tipifamib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy.

In some embodiments, the additional cancer therapeutic agent is a differentiation agent. Such differentiation agent includes retinoids (such as all-trans-retinoic acid (ATRA), 9-cis retinoic acid, 13-cis-retinoic acid (13-cRA) and 4-hydroxy-phenretinamide (4-HPR)); arsenic trioxide; histone deacetylase inhibitors HDACs (such as azacytidine (Vidaza) and butyrates (e.g., sodium phenylbutyrate)); hybrid polar compounds (such as hexamethylene bisacetamide ((HMBA)); vitamin D; and cytokines (such as colony-stimulating factors including G-CSF and GM-CSF, and interferons).

In some embodiments the additional cancer therapeutic agent is a targeted therapy agent. Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, dasatinib, erlotinib, imatinib, gefitinib, lapatinib, Lestaurtinib, Nilotinib, Semaxanib, Sorafenib, Sunitinib, and Vandetanib, and also cyclin dependent kinase inhibitors such as Alvocidib and Seliciclib. Monoclonal antibody therapy is another strategy in which the therapeutic agent is an antibody which specifically binds to a protein on the surface of the cancer cells. Examples include the anti HER2/neu antibody trastuzumab (HERCEPTIN®) typically used in breast cancer, and the anti CD20 antibody rituximab and Tositumomab typically used in a variety of B cell malignancies. Other exemplary antibodies include Cetuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a compound described herein, e.g., a biguanide such as metformin or phenformin, preferably phenformin.

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®.

In some embodiments, the additional cancer therapeutic agent is an immunotherapy agent. Cancer immunotherapy refers to a diverse set of therapeutic strategies designed to induce the subject's own immune system to fight the tumor. Contemporary methods for generating an immune response against tumors include intravesicular BCG immunotherapy for superficial bladder cancer, and use of interferons and other cytokines to induce an immune response in renal cell carcinoma and melanoma subjects.

Allogeneic hematopoietic stem cell transplantation can be considered a form of immunotherapy, since the donor's immune cells will often attack the tumor in a graft versus tumor effect. In some embodiments, the immunotherapy agents can be used in combination with a compound or composition described herein.

In some embodiments, the additional cancer therapeutic agent is a hormonal therapy agent. The growth of some cancers can be inhibited by providing or blocking certain hormones. Common examples of hormone sensitive tumors include certain types of breast and prostate cancers. Removing or blocking estrogen or testosterone is often an important additional treatment. In certain cancers, administration of hormone agonists, such as progestogens may be therapeutically beneficial. In some embodiments, the hormonal therapy agents can be used in combination with a compound or a composition described herein.

Other possible additional therapeutic modalities include imatinib, gene therapy, peptide and dendritic cell vaccines, synthetic chlorotoxins, and radiolabeled drugs and antibodies.

In one embodiment, the compositions provided herein are used for treatment of AML in combination with an AML induction and consolidation therapy. In one embodiment, the AML induction therapy is a combination of cytarabine and daunorubicin. In one embodiment, the AML induction therapy is a combination of cytarabine and idarubicin.

In one embodiment, the AML consolidation therapy is cytarabine. In one embodiment, the AML consolidation therapy is a combination of mitoxantrone and etoposide.

In one embodiment, the compositions provided herein are used in combination with one or more DNA demethylating agents. In one embodiment, the DNA demethylating agent is a cytidine analog. In certain embodiments, the cytidine analog is azacitidine or 5-aza-2'-deoxycytidine (decitabine). In certain embodiments, the cytidine analog is azacitidine. In certain embodiments, the cytidine analog is 5-aza-2'-deoxycytidine (decitabine). In certain embodiments, the cytidine analog is, for example: 1-β-D-arabinofuranosylcytosine (cytarabine or ara-C); pseudoiso-cytidine (psi ICR); 5-fluoro-2'-deoxycytidine (FCdR); 2'-deoxy-2',2'-difluorocytidine (gemcitabine); 5-aza-2'-deoxy-2',2'-difluorocytidine; 5-aza-2'-deoxy-2'-fluorocytidine; 1-β-D-ribofuranosyl-2(1H)-pyrimidinone (zebularine); 2',3'-dideoxy-5-fluoro-3'-thiacytidine (emtriva); 2'-cyclocytidine (ancitabine); 1-β-D-arabinofuranosyl-5-azacytosine (fazarabine or ara-AC); 6-azacitidine (6-aza-CR); 5,6-dihydro-5-azacitidine (dH-aza-CR); $N^4$ pentyloxy-carbonyl-5'-deoxy-5-fluorocytidine (capecitabine); $N^4$ octadecyl-cytarabine; or elaidic acid cytarabine. In certain embodiments, the cytidine analogs include any compound which is structurally related to cytidine or deoxycytidine and functionally mimics and/or antagonizes the action of cytidine or deoxycytidine.

In one embodiment, the compositions provided herein are used in combination with azacitidine.

In one embodiment, the compositions provided herein are used in combination with a FLT3 inhibitor. In one embodiment, the FLT3 inhibitor is selected from quizartinib (AC220), sunitinib (SU11248), sorafenib (BAY 43-9006), midostaurin (PKC412), crenolanib (CP-868596), PLX3397, E6201, AKN-028, ponatinib (AP24534), ASP2215, KW-2449, famitinib and DCC-2036.

In one embodiment, the compositions provided herein are used in combination with MEK kinase inhibitor. In one embodiment, the MEK kinase is selected from trametinib, selumetinib, binimetinib, PD-325901, cobimetinib, CI-1040 and PD035901.

In one embodiment, the compositions provided herein are used in combination with a JAK inhibitor. In one embodiment, the compositions provided herein are used in combination with a JAK2 inhibitor. In one embodiment, the JAK2 inhibitor is selected from INCB018424 (ruxolitinib), TG101348, CYT387, AZD1480, SB1518 (pacritinib), XL019, NCBO-16562, NVP-BSK805, R723, hydroxycarbamide, SAR302503, CP-690,550 (tasocitinib) and INCB16562. In one embodiment, the compositions provided herein are used in combination with ruxolitinib.

EXAMPLES

The embodiments described below are intended to be merely exemplary, and those skilled in the art will recognize, or will be able to ascertain using no more than routine experimentation, numerous equivalents of specific compounds, materials, and procedures. All such equivalents are considered to be within the scope of the claimed subject matter and are encompassed by the appended claims.

2-Methyl-1-[(4-[6-(trifluoromethyl)pyridin-2-yl]-6-{[2-(trifluoromethyl)pyridin-4-yl]amino}-1,3,5-triazin-2-yl) amino]propan-2-ol methanesulfonate was prepared by methods known in the art, for example, US Publication No. US-2013/0190287, U.S. Provisional Application No. 62/201,546, International Publication Nos. WO 2015/018060 and WO 2015/017821 and International Application No. PCT/US2016/016335.

Example 1: Synthesis of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol Example 1, Step 1: Preparation of 6-trifluoromethyl-pyridine-2-carboxylic acid Diethyl ether (4.32 L) and hexanes (5.40 L) were added to the reaction vessel under $N_2$ atmosphere, and cooled to −75° C. to −65° C. Dropwise addition of n-Butyl lithium (3.78 L in 1.6 M hexane) under $N_2$ atmosphere at below −65° C. was followed by dropwise addition of dimethyl amino ethanol (327.45 g, 3.67 mol) and after 10 min. dropwise addition of 2-trifluoromethyl pyridine (360 g, 2.45 mol). The reaction was stirred under $N_2$ while maintaining the temperature below −65° C. for about 2.0-2.5 hrs. The reaction mixture was poured over crushed dry ice under $N_2$, then brought to a temperature of 0 to 50° C. while stirring (approx. 1.0 to 1.5 h) followed by the addition of water (1.8 L). The reaction mixture was stirred for 5-10 mins and allowed to warm to 5-10° C. 6N HCl (900 mL) was added dropwise until the mixture reached pH 1.0 to 2.0, then the mixture was stirred for 10-20 min. at 5-10° C. The reaction mixture was diluted with ethyl acetate at 25-35° C., then washed with brine solution. The reaction was concentrated and rinsed with n-heptane and then dried to yield 6-trifluoromethyl-pyridine-2-carboxylic acid.

Example 1, Step 2: Preparation of 6-trifluoromethyl-pyridine-2-carboxylic acid methyl ester Methanol was added to the reaction vessel under nitrogen atmosphere. 6-trifluoromethyl-pyridine-2-carboxylic acid (150 g, 0.785 mol) was added and dissolved at ambient temperature. Acetyl chloride (67.78 g, 0.863 mol) was added dropwise at a temperature below 45° C. The reaction mixture was maintained at 65-70° C. for about 2-2.5 h, and then concentrated at 35-45° C. under vacuum and cooled to 25-35° C. The mixture was diluted with ethyl acetate and rinsed with saturated $NaHCO_3$ solution then rinsed with brine solution. The mixture was concentrated at 35-45° C. under vacuum and cooled to 25-35° C., then rinsed with n-heptane and concentrated at 35-45° C. under vacuum, then degassed to obtain brown solid, which was rinsed with n-heptane and stirred for 10-15 minute at 25-35° C. The suspension was cooled to −40 to −30° C. while stirring, and filtered and dried to provide 6-trifluoromethyl-pyridine-2-carboxylic acid methyl ester.

Example 1, Step 3: Preparation of 6-(6-trifluoromethyl-pyridin-2-yl)-1H-1,3,5-triazine-2,4-dione 1 L absolute ethanol was charged to the reaction vessel under $N_2$ atmosphere and sodium metal (11.2 g, 0.488 mol) was added in portions under $N_2$ atmosphere at below 50° C. The reaction was stirred for 5-10 minutes, then heated to 50-55° C. Dried Biuret (12.5 g, 0.122 mol) was added to the reaction vessel under $N_2$ atmosphere at 50-55° C. temperature, and stirred for 10-15 minutes. While maintaining 50-55° C. 6-trifluoromethyl-pyridine-2-carboxylic acid methyl ester (50.0 g, 0.244 mol) was added. The reaction mixture was heated to reflux (75-80° C.) and maintained for 1.5-2 hours, then cooled to 35-40° C., and concentrated at 45-50° C. under vacuum. Water was added and the mixture was concentrated under vacuum then cooled to 35-40° C., more water was added and the mixture was cooled to 0-5° C. pH was adjusted to 7-8 by slow addition of 6N HCl, a solid precipitated which was centrifuged and rinsed with water and centrifuged again. The off white to light brown solid of 6-(6-trifluoromethyl-pyridin-2-yl)-1H-1,3,5-triazine-2,4-dione was dried under vacuum for 8 to 10 hrs at 50° C. to 60° C. under 600 mm/Hg pressure to provide 6-(6-trifluoromethyl-pyridin-2-yl)-1H-1,3,5-triazine-2,4-dione.

Example 1, Step 4: Preparation of 2, 4-dichloro-6-(6-trifluoromethyl-pyridin-2-yl)-1, 3, 5-triazine $POCl_3$ (175.0 mL) is charged into the reaction vessel at 20-35° C., and 6-(6-trifluoromethyl-pyridin-2-yl)-1H-1,3,5-triazine-2,4-dione (35.0 g, 0.1355 mol) was added in portions at below 50° C. The reaction mixture was de-gassed 5-20 minutes by purging with $N_2$ gas. Phosphorous pentachloride (112.86 g, 0.542 mol) was added while stirring at below 50° C., the resulting slurry was heated to reflux (105-110° C.) and maintained for 3-4 h. The reaction mixture was cooled to 50-55° C., concentrated at below 55° C. then cooled to 20-30° C. The reaction mixture was rinsed with ethyl acetate and the ethyl acetate layer was slowly added to cold water (temperature −5° C.) while stirring and maintaining the temperature below 10° C. The mixture was stirred 3-5 minutes at a temperature between 10 to 20° C. and the ethyl acetate layer was collected. The reaction mixture was rinsed with sodium bicarbonate solution and dried over anhydrous sodium sulphate. The material was dried 2-3 h under vacuum at below 45° C. to provide 2, 4-dichloro-6-(6-trifluoromethyl-pyridin-2-yl)-1, 3, 5-triazine.

Example 1, Step 5: Preparation of 4-chloro-6-(6-(triuoromethyl)pyridin-2-yl)-N-(2-(trifluoromethyl)-pyridin-4-yl)-1,3,5-triazin-2-amine A mixture of THF (135 mL) and 2,4-dichloro-6-(6-trifluoromethyl-pyridin-2-yl)-1, 3, 5-triazine (27.0 g, 0.0915 mol) were added to the reaction vessel at 20-35° C., then 4-amino-2-(trifluoromethyl)pyridine (16.31 g, 0.1006 mol) and sodium bicarbonate (11.52 g, 0.1372 mol) were added. The resulting slurry was heated to reflux (75-80° C.) for 20-24 h. The reaction was cooled to 30-40° C. and THF was evaporated at below 45° C. under reduced pressure. The reaction mixture was cooled to 20-35° C., rinsed with ethyl acetate and water, and the ethyl acetate layer was collected and rinsed with 0.5 N HCl and brine solution. The organic layer was concentrated under vacuum at below 45° C., then rinsed with dichloromethane and hexanes, filtered and washed with hexanes and dried for 5-6 h at 45-50° C. under vacuum to provide 4-chloro-6-(6-(trifluoromethyl)pyridin-2-yl)-N-(2-(trifluoro-methyl)-pyridin-4-yl)-1,3,5-triazin-2-amine.

Example 1, Step 6: Preparation of 2-methyl-1-(4-(6-(trifluoromethyl)pyridin-2-yl)-6-(2-(trifluoromethyl)-pyridin-4-ylamino)-1,3,5-triazin-2-ylamino) propan-2-ol THF (290 mL), 4-chloro-6-(6-(trifluoromethyl)pyridin-2-yl)-N-(2-(trifluoro-methyl)-pyridin-4-yl)-1,3,5-triazin-2-amine (29.0 g, 0.06893 mol), sodium bicarbonate (8.68 g, 0.1033 mol), and 1,1-dimethylaminoethanol (7.37 g, 0.08271 mol) were added to the reaction vessel at 20-35° C. The resulting slurry was heated to reflux (75-80° C.) for 16-20 h. The reaction was cooled to 30-40° C. and THF was evaporated at below 45° C. under reduced pressure. The reaction mixture was cooled to 20-35° C., rinsed with ethyl acetate and water, and the ethyl acetate layer was collected. The organic layer was concentrated under vacuum at below 45° C. then rinsed with dichloromethane and hexanes, filtered and washed with hexanes and dried for 8-10 h at 45-50° C. under vacuum to provide 2-methyl-1-(4-(6-(trifluoromethyl)pyridin-2-yl)-6-(2-(trifluoromethyl)-pyridin-4-ylamino)-1,3,5-triazin-2-ylamino)propan-2-ol.

Example 2: Synthesis of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate Acetone (435.0 mL) and 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol (87.0 g, 0.184 mol) were added to the reaction vessel at 20-35° C. In a separate vessel, methanesulfonic acid was added over 10 minutes to cold (0-4° C.) acetone (191.4 mL) while stirring to prepare a methane sulfonic acid solution. While passing through a micron filter, the freshly prepared methanesulfonic acid solution was added dropwise to the reaction mixture. The resulting slurry was filtered using nutsche filter and washed with acetone. The filtered material was dried for 30-40 minutes using vacuum to provide 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate.

Example 3: Synthesis of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate Form 3

Crystallization to Form 3 was accomplished via the following salt formation: 1) acetone (500 ml, 4.17 vol) was charged to the crystallizer, then the mixture was agitated (550 rpm) for 10 min., 2) 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol (120.0 g, 253.5 mmol) was charged into crystallizer via solid charger over 45 min., 3) the solid charger was rinsed with acetone (100 ml, 0.83 vol), 4) the reaction was stirred (550 rpm) and heated to 35° C. to obtain a clear solution (in 10 min), 5) a first portion (2%) of MSA/acetone solution (0.3 mol/L, 18.1 ml, 3.8 ml/min) was added over 5 min via a piston pump, then the pump pipeline was washed with acetone (5 ml, 0.04 vol), 6) the mixture was aged at 35° C. for 10 to 15 min, while ensuring the solution remained clear, 7) 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate seed (2.4 g as generated in Example 2, 2 wt %) was added to the clear solution, 8) a second portion (49%) of MSA/acetone solution (0.3 mol/L, 444 ml, 3.7 ml/min) was added over 2 hrs, 9) the mixture was aged at 35° C. for 30 min, 10) a third portion (49%) of MSA/acetone solution (0.3 mol/L, 444 ml, 7.4 ml/min) was added over 1 hr, 11) the mixture was aged at 35° C. for 2 hr, 12) the mixture was cooled to 20° C. for 1 hr, 13) the mixture was filtered and the cake washed with acetone (240 ml twice), 17) and dried under vacuum at 30° C.; to provide Form 3 crystals.

Example 4: Preparation of Coated Tablets

Table 1 below provides details of excipients used in the manufacture of the coated tablets. All excipients comply with USP/NF/Ph. Eur. Monographs, unless stated or otherwise requested.

TABLE 1

Compound and excipients used in feasibility manufacturing

| Excipients | Commercial grade |
| --- | --- |
| 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate | N/A |
| Microcrystalline cellulose PH 102 | Avicel PH 102 |
| HPC-EXF | LH-11 |
| Hypromellose Acetate Succinate (HPMC-AS) | AS-MF |
| Sodium Starch Glycolate | Primojel |
| Colloidal Silicon Dioxide | Cab-O-Sil |
| Sodium Lauryl Sulphate | n/a |
| Magnesium stearate (non-bovine) | n/a |
| Opadry II | OPADRY |

The tablet formulations described below were prepared and tested to:

evaluate and compare different types of compression tooling with respect to their shape, material of construction and surface coating/treatment;

evaluate process parameters during granulation (roller compaction and milling) and compression;

evaluate formulation composition with respect to lubricant and glidant concentrations used intra- vs. extragranularly; and evaluate effect of coating on tablet dissolution profiles.

Figure 5:
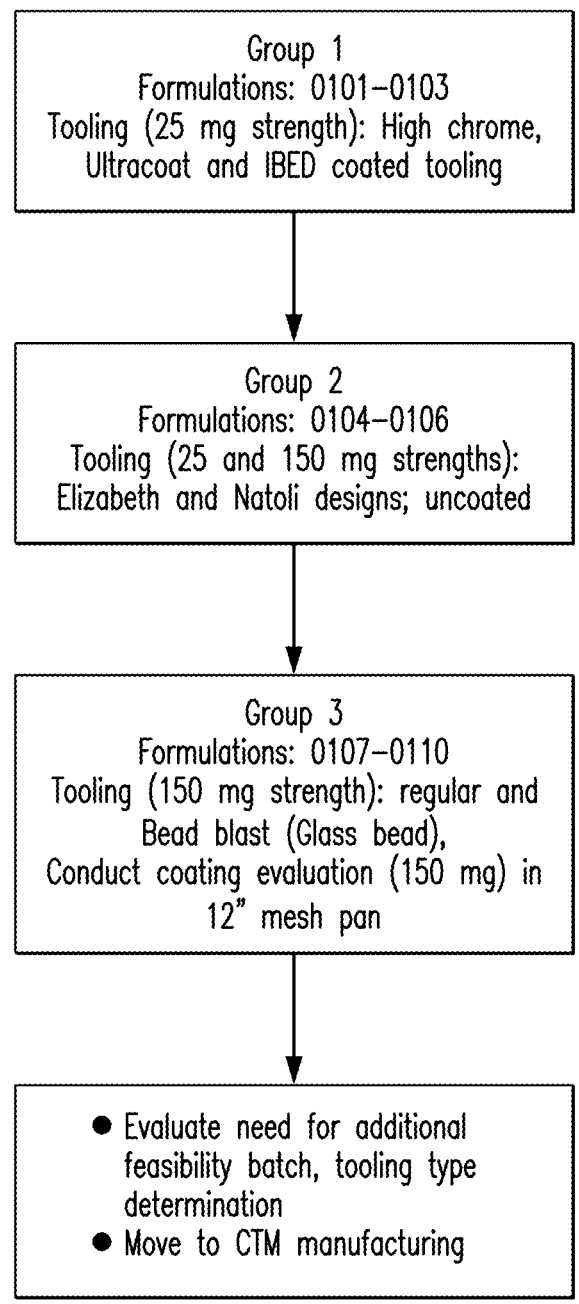
FIG. 5 illustrates a process development plan for making 25 and 150 mg tablets.

The tablet formulations are divided into three groups as described below. FIG. 5 illustrates a process development plan for feasibility of 25 mg and 150 mg strength tablets in the three groups.

Group 1

In Group 1 (Formulations 0101 to 0103), the formulations were evaluated for compression of 25 mg tablets with tooling of various coatings or treatments on an instrumented 10 station Piccola single layer tablet press. The following tooling were compared:

Chromium Nitride Ultra Coat from Natoli—coated by an electrolytic process;

Chromium Nitride-IBED coated by Beamalloy Technologies, LLC—coated by ion beam enhanced deposition method;

M340 steel—High Chromium content steel; and

Standard, 6 mm round, plain faces.

The press was equipped with 2 sets of each tooling type for a maximum of six compression stations, depending on tooling used. Runs with standard, 6 mm round punches (FD-304) were set up with only two stations. A set-up run was performed to achieve target tablet weight and hardness following which the run was continued with intermittent evaluation of punch surfaces for any kind of film formation. Process parameters evaluated were:

1. Pre-compression Evaluation: Initial press "set-up" activities were performed utilizing pre-compression with clean tooling. The run was continued with intermittent evaluation of punch surfaces.

2. Elevated Main Compression: Press "set-up" was performed utilizing pre-compression (if applicable); however, for the first five revolutions of compression set the main compression force approaching the maximum force tip rating (NMT 10% of the maximum force specified on the tooling drawings) was used. Tablets were intentionally compressed above specification with respect to tablet hardness to evaluate the impact of compression force on the film formation. After five revolutions, the main compression force was reduced to achieve target tablet hardness. The run was continued with intermittent evaluation of punch surfaces.

3. Elevated Main Compression w/o Pre-compression: Experiment similar to the process above was repeated but without using any pre-compression force.

As listed in Table 2 (Batch Nos. 25 mg 0101 to 25 mg 0301) different formulation batches were produced to determine the effect of minor adjustments to the intra-granular and extra-granular composition of magnesium stearate and/or colloidal silicon dioxide.

Group 2

In Group 2, formulations 0104-0106 were evaluated with the following tooling:

Standard 6 mm round, plain tooling (25 mg strength);

0.624"×0.3268" capsule-shaped plain (150 mg strength); and 0.624"×0.3268" IBED-treated (150 mg strength).

Pre-compression force was increased in formulation 4 and 5 up to 75% to determine effect on punch filming and sticking.

In Group 2, formulations were roller compacted with a change in excipient composition. In the extra-granular composition, MCC PH102 was decreased, while magnesium stearate amount was increased to increase lubrication. A comparison of compaction force was also tested in formulation 4 with two screen sizes (0.8 and 1.25 mm) to determine the effect on particle size distribution.

Group 3

In Group 3 (Formulations 0107 to 0110), formulations with higher extra-granular MCC PH102 were compared, with reduced drug load or intra-granular MCC PH102. The 150 mg strength tablets were compressed using the following tooling:

0.624"×0.3268" capsule-shaped, bead blasted punches by Natoli;

0.643"×0.337" capsule-shaped, plain by Elizabeth Carbide (also abbreviated EC);

0.643"×0.337" capsule-shaped, plain by EC; and 0.643"×0.337" capsule-shaped, bead blasted punches by EC Formulation 0110 was processed by increasing main compression forces, and samples were collected to determine effect on tablet dissolution.

Table 2 summarizes compositions for the coated tablets for formulations 0101-0110 (designated as 0101-0110). Table 3 provides summary of tooling and process parameters studied during various trials and the respective observations.

TABLE 2

Compositions for Coated Tablets

| No | Ingredient | 25 mg 0101 | 25 mg 0102 | 25 mg 0103 | 5 mg 0104 | 25 mg 0105 | 25 mg 0106 | 5 mg 0107 | 25 mg 0108 | 25 mg 0109 | 25 mg 0110 |
|---|---|---|---|---|---|---|---|---|---|---|---|
| | | | Group 1 | | | Group 2 | | | | Group 3 | |
| | Intra-granular (% w/w) | | | | | | | | | | |
| 1 | 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate | 30.0 | 30.0 | 30.0 | 30.0 | 30.0 | 30.0 | 30.0 | 20.0 | 30.0 | 20.0 |
| 2 | Microcrystalline Cellulose PH 102 | 40.0 | 40.0 | 40.0 | 45.0 | 45.0 | 55.5 | 45.0 | 44.5 | 34.5 | 44.5 |
| 3 | Hydroxypropyl Cellulose (EXF) | 2.0 | 2.0 | 2.0 | 2.0 | 2.0 | 2.0 | 2.0 | 2.0 | 2.0 | 2.0 |
| 4 | Sodium Starch Glycolate | 6.0 | 6.0 | 6.0 | 6.0 | 6.0 | 6.0 | 6.0 | 6.0 | 6.0 | 6.0 |
| 5 | Sodium Lauryl Sulfate | 1.0 | 1.0 | 1.0 | 1.0 | 1.0 | 1.0 | 1.0 | 1.0 | 1.0 | 1.0 |
| 6 | Hypromellose Acetate Succinate (HPMC AS_MF) | 1.0 | 1.0 | 1.0 | 1.0 | 1.0 | 1.0 | 1.0 | 1.0 | 1.0 | 1.0 |
| 7 | Colloidal Silicon Dioxide | 1.5 | 1.5 | 0.75 | 1.5 | 1.5 | 0.75 | 1.5 | 1.5 | 1.5 | 1.5 |
| 8 | Magnesium Stearate | 0.75 | 0.25 | 0.25 | 0.75 | 0.25 | 1.0 | 0.75 | 0.75 | 0.75 | 0.75 |
| | Extra-granular (% w/w) | | | | | | | | | | |
| 9 | Microcrystalline Cellulose PH 102 | 14.5 | 14.5 | 14.5 | 9.5 | 9.5 | — | 9.5 | 20.0 | 20.0 | 20.0 |

TABLE 2-continued

Compositions for Coated Tablets

| No | Ingredient | 25 mg 0101 | 25 mg 0102 | 25 mg 0103 | 5 mg 0104 | 25 mg 0105 | 25 mg 0106 | 5 mg 0107 | 25 mg 0108 | 25 mg 0109 | 25 mg 0110 |
|---|---|---|---|---|---|---|---|---|---|---|---|
| | Batch Number | | Group 1 | | | Group 2 | | | Group 3 | | |
| 10 | Sodium Starch Glycolate | 2.0 | 2.0 | 2.0 | 2.0 | 2.0 | 2.0 | 2.0 | 2.0 | 2.0 | 2.0 |
| 11 | Colloidal Silicon Dioxide | 0.5 | 0.5 | 1.25 | 0.5 | 0.5 | — | 0.5 | 0.5 | 0.5 | 0.5 |
| 12 | magnesium Stearate | 0.75 | 1.25 | 1.25 | 0.75 | 1.25 | 1.25 | 0.75 | 0.75 | 0.75 | 0.75 |

TABLE 3

Summary of tooling and process parameters studied during feasibility trials

| Batch No. | Compression Tooling | Roller Force (kN/cm) | Granulator Screen (mm) | Pre-Compression force (%) | Compression Force (kN) | Ejection Force (N) | Observation (compression) |
|---|---|---|---|---|---|---|---|
| 25 mg 0101 | 0.25" round (fd-302 High chrome, fd-303 Ultracoat and IBED coated) | 5.2 | 0.8 | 0-50 | 10-12 | | Filming observed on the punch surfaces (IBED>Ultracoat>High chrome) |
| 25 mg 0101-A | 0.25" round (fd-302 High chrome, fd-303 Ultracoat and IBED coated) | 5.2 | 0.8 | 0 | 11.4-12.4 | | |
| 25 mg 0102 | 0.25" round (fd-302 High chrome, fd-303 Ultracoat and IBED coated) | 5.2 (0-8 min) | 0.8 | 0-100 | 10.4-11.2 | | |
| 25 mg 0102-A | 6 mm round FD-304 (EC tooling) | 3.0 | 0.8 | 0 | 10.3-11.1 | 75.9-78.2 KN | Press speed increased from 15 RPM to 45 RPM at 35 mm. No filming or capping observed |
| 25 mg 0103 | 0.25 mm round (fd-302 High chrome, fd-303 Ultracoat and IBED coated) | 5.2 | 0.8 | N/A | 10.8-11.4 | | 45 mm run time at 15 rpm. |
| 25 mg 0104 | Fd-304 EC 6 mm round- also tested isometric and fd-302 high chrome | 3.0 | 0.8 | N/A | 10.5-16 | | For Elizabeth tooling no filming after 45 min at 50 rpm, 3-4 capped tablets were found while running at 50 rpm. For Natoli high chrome and isometric tooling, filming and capping observed EC High Chrome ran for 44 min at 50 rpm. Light filming on tooling edges. Tablets appeared dull. |
| 25 mg 0104A | Fd-304 EC 6 mm round | 3.0 | 1.0 | N/A | 9.5 | | Capping observed after 15 min at 50 rpm |
| 25 mg 0105A | 6mm round FD-304 (EC) 0.624 × .3268 Natoli-IBED | 3.0 | 0.8 | NA | 9.1 | | Filming observed within 5 min run wit Natoli-IBED tooling. Run discontinued. |
| 25 mg 0105B | 0.624 × .3268 EC 0.624 × .3268 Natoli-IBED | 3.0 | 1.0 | 75 | 15-18.1 | | Capping and minor filiming observed with EC. Heavy filming observed with Natoli tooling. |
| 25 mg 0106 | 0.6240 × 0.3268 Natoli Bead Blast | 3.0 | 1.0 | | | | |
| 25 mg 0107 | | 3.0 | 1.0 | 0-50 | 14-18.7 | | Filming observed after 15 min. Capping tendency at 50% Pre-compression. |
| 25 mg 0107B | EC tooling 0.643 × .337 regular finish 0.029" and 0.034" concavity | 3 | 1.0 | | 17-18 | NA | No capping at ~10-15 min for both tooling. Very minor filming observed with 0.034" concavity tooling compared to 0.029". |
| 25 mg 0108 | 0.643 × .337 (Regular) 0.643 × .337 (Bead Matt finish) | 3.5 | 1.25 | 25 | 19 | NA | No filming or capping observed for both sets of tooling |
| 25 mg 0109 | 0.643 × .337 (Regular) 0.643 × .337 (Bead Matt finish) | 3.5 | 1.25 | N/A | 18.2-19.2 | 182-190 | No filming on matt finish. Very minor filming observed at the edge for regular finish. |

TABLE 3-continued

Summary of tooling and process parameters studied during feasibility trials

| Batch No. | Compression Tooling | Roller Force (kN/cm) | Granulator Screen (mm) | Pre-Compression force (%) | Compression Force (kN) | Ejection Force (N) | Observation (compression) |
|---|---|---|---|---|---|---|---|
| 25 mg 0109 | 0.6240 × 0.3268 Natoli Bead Blast | 3.5 | 1.25 | N/A | 17-19 | | Capping observed |
| 25 mg 0110 (205 DL) | EC - 31796-AR2: 0.643 × .337 (Regular) 0.643 × .337 (Bead Matt finish) | 3.5 | 1.25 | 30-50 | 18 | NA | Compression speed 40 rpm, no filming or capping observed. |

* DL (drug Load) is 30% unless specified

Table 4 provides a comparison of tooling types and effect on punch surfaces:

TABLE 4

| | Tooling Type | Filming | Capping | Tooling shape |
|---|---|---|---|---|
| 25 mg Tablets | Standard, Plain Round tooling 6 mm EC (Set#: FD-304) | ++ | ++ | Round |
| | Chromium Nitride-IBED coated by Beamalloy, 0.25" round (Set#: FD-305) | +++ | +++ | Round |
| | M340 High Chromium Steel, 0.25" round (Set#: FD-302) | + | + | Round |
| | Chromium Nitride Ultra Coat by Natoli, 0.25" round (Set#: FD-303) | ++ | None | Round |
| 150 mg Tablets | Chromium Nitride-IBED coated by Beamalloy, 0.624" × 0.3268" | +++ | +++ | Capsule |
| | Standard, Plain 0.643" × 0.337" Capsule tooling EC | + | None | Capsule |
| | Bead Blasted by Natoli, 0.643" × 0.337" Capsule Tooling | ++ | ++ | Capsule |
| | Standard, Plain 0.643" × 0.337" Capsule Tooling EC #31803 | ++ | None | Capsule |
| | Bead Matte finish, 0.643" × 0.337" Capsule Tooling | None | None | Capsule |

Figure 6:
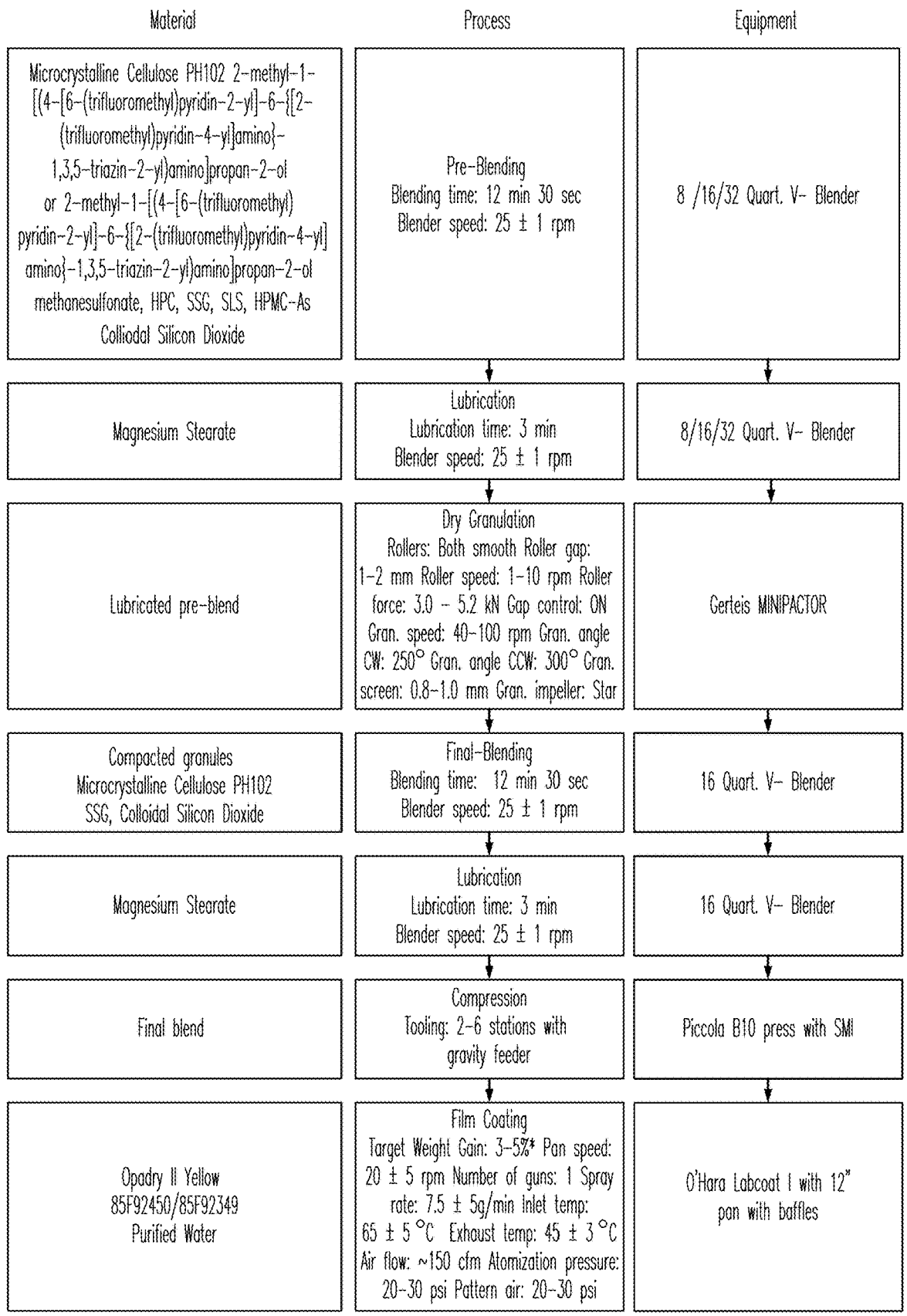
FIG. 6 provides a process flow chart for making coated tablets.

A general process flow chart outlining the manufacturing process is provided in FIG. 6. A summary of equipments used in the process is provided in Table 5.

TABLE 5

| Equipment List | |
|---|---|
| Process | Equipment |
| Compaction | Gerteis Minipactor Smooth Roller Oscillating mill PK Blender Drive O'Hara Drive 8 qt. V-Shell 16 qt. V-Shell 32 qt. V-Shell Smooth Rollers Tabletop/Floor balances |
| Compression | Piccola Single Layer Tablet Press M340 High Chromium Steel, 0.25" round Chromium Nitride Ultra Coat, 0.25" round (Natoli) Standard, Plain Round tooling, 6 mm (EC) Chromium Nitride-IBED coated tooling, 0.25" round (Beamalloy) Caliper Tabletop/Floor balances |
| Coating | Disintegration apparatus Friability Tester Hardness tester O'Hara Lab coat I 12" Coating Pan Caframo Mixer Peristaltic Pump Infrared Thermometer Tabletop/Floor balances |

Complete manufacturing process is summarized below.

2-Methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate was bag mixed with a portion of microcrystalline cellulose and screened through #20 mesh screen and transferred to V-shell. Other intra-granular excipients were manually screened through #20 mesh screen, except magnesium stearate which was screened through #30 mesh screen and transferred to the V-shell. This mixture was blended at 25 RPM for 12 min 30 sec. Magnesium stearate previously screened through 30 #mesh screen was added to the above mixture and blending was continued for 3 more minutes at 25 RPM.

This blend was compacted (dry granulated) using Gerteis MiniPactor using smooth rollers and milled using 0.8 mm granulator screen.

The milled granules were transferred to an appropriate size V-shell for final blending. Extra-granular excipients were weight adjusted for the granulation yield and added to the milled granules. The final blending was performed for 12 min 30 seconds at 25 RPM. The extra-granular portion of magnesium stearate was added to the final blend and the lubrication blending was performed for 3 min at 25 RPM.

The final lubricated blends were then compressed using the Piccola tablet press.

The core tablets were evaluated for appearance, weight variation, hardness, thickness, disintegration, and friability.

The coating was performed on core tablets from selected batches in the Lab coat I in a 12" coating pan using an aqueous suspension of Opadry II containing 18% w/w solid content.

The pre-blend and final blend granule samples were collected for physical testing (appearance, particle size, bulk and tap density, flow properties). The ribbon samples were collected for ribbon density measurement. Samples of the tablets were collected for analytical testing.

Table 6 below provides a summary of the tests performed at granulation and compression stages:

TABLE 6

| Process Stage | Batch Description | Test Test Description | Sample Size | Location |
|---|---|---|---|---|
| Lubrication | Post Lubrication Blend | Flow Properties Bulk and tapped density Particle Size (Sieve Analysis) | 120 g (bulk and tapped density) 20 g - PSD | Preblend, granulation and final Blend |
| Compression | Uncoated tablet cores | In-process testing (weight, thickness, hardness, friability) | 25-40 tablets per compression profile | As per instructions in data sheet |
| Coating | Approx. 3-5% Weight Gain | Dissolution, Appearance | 10-20 tablets | Bulk coated tablets |

Tables 7, 8 and 9 provide results of in-process tests for 25 mg and 150 mg strength tablet formulations 0101-0110.

TABLE 7

In-Process tests for 25 mg Compression Runs (formulations 0101 to 0105A)

| | | Batch # | | | | | | | | |
|---|---|---|---|---|---|---|---|---|---|---|
| | | 25 mg 0101 | | 0101A | 25 mg 0201 | 0201A | 25 mg 0301 | 25 mg 0401 | 401A | 25 mg 0501A |
| Compression Force (kN) | | 10-10.8 | 12 | 10.5-11.0 | 11.4-12.2 | 10.4-11.2 | 10.3-11.1 | 10.8-11.4 | 10.5 | 9.5 | 9.1 |
| Precompression (%) | | Off | 50 | 100 | Off | Off | Off | Off | Off | Off | Off |
| Press speed (rpm) | | 15 | 15 | 15 | 15 | 15 -> 30 | 15 -> 45 | 15 -> 40 | 30 -> 50 | 50 | 30 |
| Avg. Tab. Wt. (mg) | | 101.8 | 100.7 | 101.7 | 100.8 | 101.2 | 101.1 | 100.7 | 100.4 | 98.9 | 101.4 |
| Ind. Tab. Wt. (mg) | Min. | 100 | 100 | 100 | 99 | 99 | 99 | 100 | 98.4 | 97.3 | 99.6 |
| | Max. | 104 | 103 | 103 | 101 | 104 | 102 | 102 | 101.1 | 100.2 | 104.2 |
| | Mean | 101.8 | 101.0 | 101.7 | 102 | 101.3 | 101.2 | 101.1 | 100.4 | 98.9 | 101.7 |
| | RSD % | 1.01 | 1.14 | 0.93 | 1.04 | 1.48 | 1.02 | 0.87 | 0.77 | 0.96 | 1.28 |
| Hardness (kp) | Min. | 4.6 | 6.2 | 5.8 | 6.6 | 6.7 | 8.5 | 6.9 | 7.7 | 6.5 | 6.5 |
| | Max. | 5.7 | 7.2 | 6.7 | 7.7 | 7.9 | 9.4 | 8.3 | 8.2 | 7.4 | 8.2 |
| | Mean | 5.11 | 6.64 | 6.24 | 7.20 | 7.15 | 8.88 | 7.57 | 8.0 | 6.96 | 7.76 |
| Thickness (min) | Min. | 3.13 | 3.10 | 3.08 | 3.08 | 3.06 | 2.85 | 3.09 | 2.91 | 2.85 | 2.90 |
| | Max. | 3.20 | 3.17 | 3.15 | 3.11 | 3.16 | 2.9 | 3.15 | 2.95 | 2.95 | 2.95 |
| | Mean | 3.17 | 3.13 | 3.13 | 3.09 | 3.11 | 2.88 | 3.12 | 2.9255 | 2.898 | 2.93 |
| Friability (%) | | 1.3 | 0.0 | 0.0 | 0.0 | 0.0 | 0.0 | 0.0 | 0.0 | 0.0 | 0.0 |
| Disintegration (mm:ss) | | n/a | 01:30 | n/a | 01:45 | 01:20 | n/a | n/a | n/a | 02:05 | 01:48 |
| Tooling Type Used | | FD-302, 303, 305 | | | FD-302, 303, 305 | | FD-304 | FD-302, 303, 305 | FD-304 | | FD-304 |

TABLE 8

In-Process tests for 150 mg Compression Runs (Formulations 0104 to 0108)

| | | Batch # | | | | | | | | | |
|---|---|---|---|---|---|---|---|---|---|---|---|
| | | 25 mg (0104) | 0104B | 25 mg (0501B) | | 25 mg (0701) | | 0701A | 0701B | | 25 mg (0801) |
| Compression Force (kN) | | 16 | 13 | 15 | 18.1 | 14 | 18 | 15 | 15.6 | 17 | 18 | 19 |
| Precompression (%) | | 75% | Off | 75% | 75% -> 50% | Off | 25 | Off | 25 | 25 | | 25 |
| Press speed (rpm) | | 30 | 30 | 30 | 30 | 30 | 30 | 50 | 30 | 30 | 50 | 40 |
| Avg. Tab. Wt. (mg) | | 602.5 | 600.0 | 598.3 | n/a | 598.4 | n/a | 601.5 | 600.95 | 607.12 | 598.69 | 596.99 | 594.68 |
| Ind. Tab. Wt. (mg) | Min. | 599.3 | n/a | 592.4 | 598 | 594.8 | | 597.4 | 597.1 | 600.7 | 596.0 | 589.0 | 586.1 |
| | Max. | 614.6 | | 605.5 | 602 | 600.7 | | 604.0 | 606.5 | 616.9 | 603.9 | 605.8 | 599.6 |
| | Mean | 602.9 | | 598.3 | n/a | 598.2 | | 601.5 | 601.29 | 607.35 | 598.73 | 596.99 | 594.97 |
| | RSD % | 0.73 | | 0.69 | | 0.31 | | 0.33 | 0.49 | 0.98 | 0.44 | 0.88 | 0.70 |

TABLE 8-continued

In-Process tests for 150 mg Compression Runs (Formulations 0104 to 0108)

| | | Batch # | | | | | | | | | |
|---|---|---|---|---|---|---|---|---|---|---|---|
| | | 25 mg (0104) | 0104B | 25 mg (0501B) | 25 mg (0701) | | 0701A | | 0701B | 25 mg (0801) | |
| Hardness (kp) | Min. | 13.3 | n/a | 14.5 | 13.3 | 17.5 | 14.8 | 14.3 | 14.3 | 13.2 | 15.3 | 15.4 |
| | Max. | 16.9 | | 15.0 | 16.5 | 20.0 | 17.4 | 15.6 | 16.6 | 14.5 | 18.4 | 18.5 |
| | Mean | 15.45 | 14.8 | n/a | 15.44 | 18.91 | 15.87 | 14.93 | 15.46 | 13.92 | 17.46 | 17.29 |
| Thickness (mm) | Min. | 4.98 | 5.50 | | 4.89 | 4.78 | 4.91 | 4.63 | 4.73 | 4.72 | 4.73 | 4.60 |
| | Max. | 5.03 | 5.58 | | 4.93 | 4.84 | 4.98 | 4.67 | 4.79 | 4.74 | 4.77 | 4.66 |
| | Mean | 4.99 | 5.527 | | 4.906 | 4.811 | 4.938 | 4.64 | 4.76 | 4.732 | 4.75 | 4.634 |
| Friability (%) | | 0.0, 0.43 @ 12 min | 0.0, 0.66% @12 min | n/a | 0.1, 0.5 @ 12 min | | 0.3 | n/a | 0.3 | 0.0 | 0.0 | 0.0 | 0.0 | 0.0 |
| Disintegration (mm:ss) | | n/a | n/a | n/a | n/a | | n/a | | n/a | n/a | n/a | |
| Tooling Used | | 0.624 × 0.3268 Beamalloy | 0.624 × 0.3268 Beam alloy | 0.624 × 0.3268 Beamalloy, EC | 0.624 × 0.3268 Bead Matt | | 0.643 × 0.337 EC | | 0.643 × 0.337 EC | 0.643 × 0.337 EC, Bead matte | |

TABLE 9

In-Process tests for 150 mg Compression Runs (Formulations 0109 to 0110)

| | | Batch # | | | |
|---|---|---|---|---|---|
| | | 25 mg 0109 | 0109B | 25 mg 0110 | |
| Compression Force (kN) | | 18.2 | 19.2 | 18.5-19 | 18 |
| Precompression (%) | | Off | Off | Off | |
| Press speed (rpm) | | 30 | 40 | 32.5 | 40 |
| Avg. Tab. Wt. (mg) | | 598.8 | 599.1 | 599.87 | 605.45 | 605.6 |
| Ind. Tab. Wt. (mg) | Min. | 593.8 | 594.2 | 598.8 | 598.3 | 597.9 |
| | Max. | 602.6 | 602.2 | 607.9 | 609.4 | 609.6 |
| | Mean | 598.7 | 599.1 | 604.07 | 605.33 | 605.41 |
| | RSD % | 0.49 | 0.41 | 0.56 | 0.65 | 0.63 |
| Hardness (kp) | Min. | 16.5 | 15.3 | 13.3 | 15.5 | 14.9 |
| | Max. | 18.0 | 17.5 | 17.5 | 17.6 | 16.7 |
| | Mean | 16.94 | 16.71 | 15.79 | 16.61 | 16.02 |
| Thickness (mm) | Min. | 4.60 | 4.62 | 4.61 | 4.69 | 4.70 |
| | Max. | 4.64 | 4.66 | 4.64 | 4.71 | 4.72 |
| | Mean | 4.62 | 4.63 | 4.626 | 4.704 | 4.712 |
| Friability (%) | | 0.0 | n/a | 0.0 | 0.0 | 0.0 |
| Disintegration (mm:ss) | | n/a | | | 02:10 | 02:06 |
| Tooling Type Used | | 0.643 × 0.337 EC, Bead matte | | 0.643 × 0.337 Bead matte | 0.643 × 0.337 EC, Bead matte | |

Table 10 below provides process parameters for the coating step

TABLE 10

| | Tablets Batches | | |
|---|---|---|---|
| Parameter | 25 mg 0102 | 25 mg 0109 | 25 mg 0110 |
| Coating Pan size, Mesh Pan, inch | 12 | 12 | 12 |
| Pan load, kg | 1.1 | 1.0 | 1.0 |
| Pan speed, rpm Range: 5-25* | 20 | 17 | 17-18 |
| Atomizing Air, psi Range: 5-25* | 25 | 18 | 18 |
| Pattern Air, psi Range: 5-15* | 25 | 25 | 25 |
| Supply Air Volume range, cfm Range: 145-175 | 150-154 | 150-154 | 150-154 |
| Gun to Bed Distance, inch Range: 4-6 Inch | 4.5 | 4.5 | 4.5 |
| Inlet Air Temperature during the coating, ° C. Range: 50-70° C. | 55.3-66.4 | 56.1-65.2 | 58.3-65.2 |
| Exhaust Air Temperature during coating, ° C. Range: 42-54° C. | 45.1-46.1 | 45.3-45.4 | 45.3-46.0 |
| Spray Rate, g/min Target: 6 g/min | 7.4-8.2 | 7.6 | 7.3-8.3 |
| Total Spraying Time (hh:mm:ss) | 0:45:00 | 0:33:00 | 0:34:00 |
| Amount of Coating suspension sprayed, g | 344.7 | 250.8 | 272.0 |
| Coated Tablet Weight Gain after drying (% w/w) (Mean) | 4.1 | 4.0 | 4.1 |

Table A below provides exemplary tablet formulations.

TABLE A

| | Component | 30% Drug load Weight Composition (%) "Formulation 2" | 30% Drug Load Weight Composition (%) "Formulation 2" Modified | 20% Drug Load Weight Composition (%) | 25% Drug Load Weight Composition (%) "Formulation 3" |
|---|---|---|---|---|---|
| Intragranular | 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate | 30.00 | 30.00 | 20.00 | 25.00 |
| | Microcrystalline Cellulose (Avicel Type PH-102) | 45.00 | 34.50 | 44.50 | 39.50 |
| | Hydroxypropyl Cellulose (Klucel EXF PHARM) | 2.00 | 2.00 | 2.00 | 2.00 |
| | Sodium Starch Glycolate | 6.00 | 6.00 | 6.00 | 6.00 |
| | Sodium Lauryl Sulfate | 1.00 | 1.00 | 1.00 | 1.00 |

TABLE A-continued

|  | Component | 30% Drug load Weight Composition (%) "Formulation 2" | 30% Drug Load Weight Composition (%) "Formulation 2" Modified | 20% Drug Load Weight Composition (%) | 25% Drug Load Weight Composition (%) "Formulation 3" |
|---|---|---|---|---|---|
|  | Hypromellose Acetate Succinate | 1.00 | 1.00 | 1.00 | 1.00 |
|  | Colloidal Silicon Dioxide (Cab-o-Sil M5P) | 1.50 | 1.50 | 1.50 | 1.50 |
|  | Magnesium Stearate (Vegetabile Grade, Hyqual) | 0.75 | 0.75 | 0.75 | 0.75 |
|  | Total Intra-Granular | 87.25 | 76.75 | 76.75 | 76.75 |
| Extragranular | Microcrystalline Cellulose (Avicel Type PH-102) | 9.50 | 20.00 | 20.00 | 20.00 |
|  | Sodium Starch Glycolate | 2.00 | 2.00 | 2.00 | 2.00 |
|  | Colloidal Silicon Dioxide (Cab-o-Sil M5P) | 0.50 | 0.50 | 0.50 | 0.50 |
|  | Magnesium Stearate (HyQual ®), | 0.75 | 0.75 | 0.75 | 0.75 |
|  | Total Extra-Granular | 12.75 | 23.25 | 23.25 | 23.25 |
|  | Total | 100.00 | 100.00 | 100.00 | 100.00 |

Example 5

The effect of compaction force on the particle size distribution and dissolution profile of 25 mg and 150 mg strength tablets was studied.

The effect of compaction force on the particle size distribution is provided in Tables 11-12. The effect of compaction force on the dissolution profile is provided in Tables 13-15.

TABLE 11

Effect of roller compaction force on the particle size distribution
(25 mg 0104/Granulator Screen 1.25 mm)

| | | | Result* | | | | | |
|---|---|---|---|---|---|---|---|---|
| | | | % Retained Compaction Force (kN/cm) | | | | | |
| Test | Method | Sieve#/ | 1.5 kN | 2.0 kN | 2.5 kN | 3.0 kN | 4.0 kN | 5.0 kN |
| Particle size Distribution | USP<786> SOP LAB 2018 | 20 | 9.5 | 12.8 | 18.3 | 19.3 | 23.5 | 27.3 |
| | | 35 | 8.0 | 10.3 | 14.2 | 15.6 | 18.7 | 25.8 |
| | | 60 | 9.4 | 12.0 | 13.7 | 12.6 | 13.7 | 14.2 |
| | | 100 | 16.9 | 16.9 | 14.8 | 13.8 | 12.9 | 10.6 |
| | | 140 | 12.3 | 11.5 | 10.3 | 9.0 | 8.2 | 6.2 |
| | | 200 | 10.3 | 9.6 | 8.7 | 8.1 | 7.2 | 5.2 |
| | | Pan | 33.5 | 26.9 | 20.0 | 21.5 | 15.8 | 10.6 |

TABLE 12

Effect of roller compaction force on the particle size distribution
(25 mg 0104/Granulator Screen 0.8 mm)

| | | | Result | | |
|---|---|---|---|---|---|
| | | | % Retained Compaction Force (kN/cm) | | |
| Test | Method | Sieve#/ | 2.5 kN | 4.0 kN | 5.0 kN |
| Particle Size Distribution | USP<786> SOP LAB 2018 | 20 | 0.1 | 0.3 | 0.3 |
| | | 35 | 7.9 | 12.3 | 16.1 |
| | | 60 | 17.2 | 24.2 | 28.0 |
| | | 100 | 20.3 | 19.3 | 19.3 |
| | | 140 | 12.7 | 11.3 | 10.5 |
| | | 200 | 11.1 | 9.5 | 8.4 |
| | | Pan | 30.8 | 23.0 | 17.5 |

TABLE 13

Effect of compression force (hardness) on the dissolution profile 25 mg 0110, Hardness 15 kp

| | % Dissolved | | | | | | |
|---|---|---|---|---|---|---|---|
| Vessel # | 5 min | 10 min | 15 min | 30 min | 45 min | 60 min | 90 min |
| 1 | 76 | 90 | 96 | 99 | 100 | 101 | 101 |
| 2 | 76 | 91 | 95 | 99 | 99 | 100 | 100 |
| 3 | 77 | 92 | 96 | 101 | 102 | 103 | 104 |
| Mean | 76 | 91 | 96 | 100 | 100 | 101 | 102 |
| SD | 0.6 | 1.0 | 0.6 | 1.2 | 1.5 | 1.5 | 2.1 |
| % RSD | 0.8 | 1.1 | 0.6 | 1.2 | 1.5 | 1.5 | 2.0 |
| Min | 76 | 90 | 95 | 99 | 99 | 100 | 100 |
| Max | 77 | 92 | 96 | 101 | 102 | 103 | 104 |

TABLE 14

Effect of compression force (hardness) on the dissolution profile 25 mg 0110, Hardness 17 kp

| | % Dissolved | | | | | | |
|---|---|---|---|---|---|---|---|
| Vessel # | 5 min | 10 min | 15 min | 30 min | 45 min | 60 min | 90 min |
| 1 | 64 | 80 | 92 | 99 | 102 | 103 | 103 |
| 2 | 78 | 93 | 98 | 101 | 102 | 103 | 103 |
| 3 | 74 | 91 | 95 | 99 | 99 | 100 | 100 |
| Mean | 72 | 88 | 95 | 100 | 101 | 102 | 102 |
| SD | 7.2 | 7.0 | 3.0 | 1.2 | 1.7 | 1.7 | 1.7 |
| % RSD | 10.0 | 8.0 | 3.2 | 1.2 | 1.7 | 1.7 | 1.7 |
| Min | 64 | 80 | 92 | 99 | 99 | 100 | 100 |
| Max | 78 | 93 | 98 | 101 | 102 | 103 | 103 |

TABLE 15

Effect of compression force (hardness) on the dissolution profile 25 mg 0110, Hardness 18 kp

| | % Dissolved | | | | | | |
|---|---|---|---|---|---|---|---|
| Vessel # | 5 min | 10 min | 15 min | 30 min | 45 min | 60 min | 90 min |
| 1 | 64 | 81 | 92 | 99 | 101 | 101 | 102 |
| 2 | 66 | 88 | 95 | 100 | 101 | 102 | 103 |
| 3 | 59 | 82 | 92 | 98 | 100 | 101 | 101 |
| Mean | 63 | 84 | 93 | 99 | 101 | 101 | 102 |
| SD | 3.6 | 3.8 | 1.7 | 1.0 | 0.6 | 0.6 | 1.1 |
| % RSD | 5.7 | 4.5 | 1.9 | 1.0 | 0.6 | 0.6 | 1.1 |
| Min | 59 | 81 | 92 | 98 | 100 | 101 | 101 |
| Max | 66 | 88 | 95 | 100 | 101 | 102 | 103 |

As seen from data in Tables 13-15, increasing main run compression force lowered the tablet dissolution rate only in early time points (from 0 to 30 minutes) but remained unchanged past 30 minutes.

Example 6: Effect of Coating on the Dissolution Profile

The coated tablets were subjected to dissolution testing. The effect of coating on the dissolution profile is provided in Table 16 below:

TABLE 16

Effect of coating on the dissolution profile: 25 mg 0110

| | % Dissolved | | | | | | |
|---|---|---|---|---|---|---|---|
| Vessel # | 5 min | 10 min | 15 min | 30 min | 45 min | 60 min | 90 min |
| 1 | 55 | 80 | 86 | 94 | 98 | 98 | 100 |
| 2 | 53 | 80 | 87 | 92 | 96 | 99 | 102 |
| 3 | 64 | 84 | 91 | 96 | 99 | 100 | 101 |
| Mean | 57 | 81 | 88 | 94 | 98 | 99 | 101 |
| SD | 5.9 | 2.3 | 2.6 | 2.0 | 1.5 | 1.0 | 1.0 |
| % RSD | 10.2 | 2.8 | 3.0 | 2.1 | 1.6 | 1.0 | 1.0 |
| Min | 53 | 80 | 86 | 92 | 96 | 98 | 100 |
| Max | 64 | 84 | 91 | 96 | 99 | 100 | 102 |

As seen from data in Table 16, coating appears to have affected the dissolution profile mainly at early time points (5 min and 10 min) where the percent drug dissolved was noted to be slightly less as compared to that of uncoated tablets from the same batch. However, overall dissolution profile between 15 min-60 min remained unaffected and more than 90% drug was dissolved within 30 min.

Example 7: Drug Substance Form Change Studies

The drug substance lots were stored in representative commercial bulk packaging at room temperature for up to 18 months. No form change was detected for the drug substance lots.

The tablet formulations in Table 17 were used in a study to determine drug substance form change in the formulations:

TABLE 17

| | % Weight/Weight | | | |
|---|---|---|---|---|
| Formulation Component | Formulation 1a | Formulation 1b | Formulation 2 | Formulation 3 |
| mg | 5 and 10 | 50 and 200 | 50 and 100 | 50, 100, 150, and 200 |
| CC-90007 methanesulfonate | 6 | 40 | 30 | 25 |
| Microcrystalline cellulose | 80 | 44.5 | 54.5 | 59.5 |
| Hydroxypropyl cellulose | 2 | 2 | 2 | 2 |
| Sodium starch glycolate | 8 | 8 | 8 | 8 |
| Sodium lauryl sulfate | 1 | 1 | 1 | 1 |
| Hypromellose acetate succinate | 1 | 1 | 1 | 1 |
| Colloidal silicon dioxide | 1 | 2 | 2 | 2 |
| Magnesium stearate | 1 | 1.5 | 1.5 | 1.5 |
| Total core tablet | 100 | 100 | 100 | 100 |
| Film coat | NA | NA | NA | 4.0[2] |
| Total percent | 100 | 100 | 100 | 104.0 |
| Total tablet weight (mg) | 100/200 | 150/600 | 200/400 | 249.6/499.2/ 748.8/998.4 |

In the formulations of Table 17, no crystalline free base was detected using XRPD. The amorphous content (free base and methanesulfonate salt) was detected using ssNMR. The total amorphous content at time of manufacture was expected to be ≤10%.

After 24 months storage at 25° C./60% RH, Formulation 1b showed no increase in amorphous content, and no crystalline free base was detected as described in Table 18.

TABLE 18

| Strength | Time (months) | Amorphous Content (%) | Crystalline Free Base |
|---|---|---|---|
| 50 mg | 9 | ≤10 | Not Detected |
|  | 24 | ≤10 |  |
| 200 mg | 24 | ≤10 |  |

After 12 months storage at 25° C./60% RH, the amorphous content of Formulations 2 and 3 did not seem to increase, and no crystalline free base was detected as described in Tables 19 and 25, respectively.

TABLE 19

| Formulation 2: Uncoated Tablets ||||
|---|---|---|---|
| Strength | Time (months) | Amorphous Content (%) | Crystalline Free Base |
| 25 mg | Initial | ≤10 | Not Detected |
| 25 mg | 6 | ≤10 |  |
|  | 9 | ≤10 |  |
| 25 mg | 9 | ≤10 |  |
|  | 12 |  |  |
| 50 mg | 9 | ≤10 |  |
| 50 mg | 6 | ≤10 |  |
|  | 9 | ≤10 |  |
| 100 mg | 6 | ≤10 |  |
|  | 9 | ≤10 |  |
| 150 mg | 6 | ≤10 |  |
|  | 9 | ≤10 |  |

TABLE 20

| Formulation 3 - Yellow Coated Tablets ||||
|---|---|---|---|
| Strength | Time (months) | Amorphous Content (%) | Crystalline Free Base |
| 50 mg | 6 | ≤10 | Not Detected |
| 150 mg | 6 | ≤10 |  |
| 200 mg | 3 | ≤10 |  |
|  | 6 |  |  |

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed:

1. A tablet comprising 25% 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate; intra-granular excipients comprising 39.50% microcrystalline cellulose, 2% hydroxypropyl cellulose, 6% sodium starch glycolate, 1% sodium lauryl sulfate, 1% hypromellose acetate succinate, 1.5% colloidal silicon dioxide, and 0.75% magnesium stearate; and extra-granular excipients comprising 20% microcrystalline cellulose, 2% sodium starch glycolate, 0.5% colloidal silicon dioxide, and 0.75% magnesium stearate, all based on total weight of the tablet, wherein the tablet is coated with a film coating.

2. The tablet of claim 1 comprising about 25, 50, 100, 150, or 200 mg strength of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol.

3. The tablet of claim 1, wherein the tablet comprises ≤10% amorphous 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate, 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol or a mixture thereof.

4. The tablet of claim 1, wherein the tablet is coated with polyvinyl alcohol.

* * * * *